(12) United States Patent
Dorn et al.

(10) Patent No.: US 7,758,624 B2
(45) Date of Patent: Jul. 20, 2010

(54) IMPLANT DELIVERY DEVICE

(75) Inventors: Jürgen Dorn, Neulussheim (DE); Jörg Feeser, Königsbach-Stein (DE)

(73) Assignee: C. R. Bard, Inc., Murray Hill, NJ (US)

( * ) Notice: Subject to any disclaimer, the term of this patent is extended or adjusted under 35 U.S.C. 154(b) by 348 days.

(21) Appl. No.: 10/142,129

(22) Filed: May 9, 2002

(65) Prior Publication Data
US 2002/0183826 A1   Dec. 5, 2002

Related U.S. Application Data

(63) Continuation of application No. PCT/EP00/11199, filed on Nov. 13, 2000.

(51) Int. Cl.
*A61F 2/06* (2006.01)
(52) U.S. Cl. ..................................... 623/1.11
(58) Field of Classification Search ............... 606/108, 606/194, 190, 198, 192; 604/103, 103.1; 623/1.1, 1.2, 1.11, 1.12
See application file for complete search history.

(56) References Cited

U.S. PATENT DOCUMENTS

| | | |
|---|---|---|
| 3,485,234 A | 12/1969 | Stevens |
| 3,585,707 A | 6/1971 | Stevens |
| 4,516,972 A | 5/1985 | Samson |
| 4,580,568 A | 4/1986 | Gianturco |
| 4,665,918 A | 5/1987 | Garza et al. |
| 4,898,591 A | 2/1990 | Jang |
| 5,078,702 A | 1/1992 | Pomeranz |
| 5,089,006 A | 2/1992 | Stiles |
| 5,290,295 A * | 3/1994 | Querals et al. ............ 623/1.23 |
| 5,453,090 A | 9/1995 | Martinez et al. |
| 5,484,444 A | 1/1996 | Braunschweiler et al. |
| 5,603,705 A | 2/1997 | Berg |
| 5,662,703 A | 9/1997 | Yurek et al. |
| 5,674,208 A | 10/1997 | Berg et al. |
| 5,683,451 A | 11/1997 | Lenker et al. |
| 5,695,499 A | 12/1997 | Helgerson et al. |
| 5,707,376 A | 1/1998 | Kavteladze et al. |
| 5,709,702 A | 1/1998 | Cogita |
| 5,733,400 A | 3/1998 | Gore et al. |

(Continued)

FOREIGN PATENT DOCUMENTS

DE   3812188 C1   5/1989

(Continued)

*Primary Examiner*—Michael J Milano
*Assistant Examiner*—Victor X Nguyen
(74) *Attorney, Agent, or Firm*—Rutan & Tucker, LLP

(57) ABSTRACT

Disclosed is a system for delivering self-expanding stents to stenting sites within the body, which minimizes trauma to the affected tissue of the patient yet, at the same time, offers the medical practitioner a robust and simple system for stent placement. These technical effects are achieved by providing a catheter which receives the stent at its proximal end and guides it to the stenting site. The catheter serves as a guide catheter and has a tapered distal tip from which the stent emerges at the site of stenting. A stent pusher can be used which abuts the proximal end of the stent inside the guide catheter. The tapered tip can be molded and can be integral with the catheter shaft or bonded to it. The guide catheter can include a figurated portion towards its distal tip. The system has particular application to stenting the carotid artery.

6 Claims, 14 Drawing Sheets

U.S. PATENT DOCUMENTS

| | | | |
|---|---|---|---|
| 5,735,859 A * | 4/1998 | Fischell et al. ............... | 606/108 |
| 5,741,323 A | 4/1998 | Pathak | |
| 5,743,874 A | 4/1998 | Fischell et al. | |
| 5,772,669 A | 6/1998 | Vrba | |
| 5,782,855 A | 7/1998 | Lau et al. | |
| 5,792,144 A * | 8/1998 | Fischell et al. ............... | 606/108 |
| 5,817,102 A | 10/1998 | Johnson | |
| 5,824,041 A | 10/1998 | Lenker et al. | |
| 5,833,694 A * | 11/1998 | Poncet ...................... | 623/1.11 |
| 5,836,926 A | 11/1998 | Peterson et al. | |
| 5,843,090 A | 12/1998 | Schuetz | |
| 5,906,619 A | 5/1999 | Olson et al. | |
| 5,951,495 A | 9/1999 | Berg | |
| 5,951,568 A | 9/1999 | Schatz | |
| 5,957,930 A | 9/1999 | Vrba | |
| 5,980,533 A | 11/1999 | Holman | |
| 6,019,778 A | 2/2000 | Wilson et al. | |
| 6,024,763 A | 2/2000 | Lenker et al. | |
| 6,042,578 A | 3/2000 | Dinh et al. | |
| 6,042,588 A | 3/2000 | Munsinger et al. | |
| 6,042,589 A | 3/2000 | Marianne | |
| 6,120,522 A | 9/2000 | Vrba | |
| 6,126,685 A | 10/2000 | Lenker et al. | |
| 6,136,006 A | 10/2000 | Johnson | |
| 6,143,021 A | 11/2000 | Staehle | |
| 6,152,944 A * | 11/2000 | Holman et al. ............. | 623/1.11 |
| 6,212,422 B1 | 4/2001 | Berg | |
| 6,238,402 B1 | 5/2001 | Sullivan | |
| 6,241,758 B1 * | 6/2001 | Cox .......................... | 623/1.11 |
| 6,245,098 B1 * | 6/2001 | Feeser et al. ................. | 623/1.1 |
| 6,336,938 B1 | 1/2002 | Kavteladze et al. | |
| 6,368,344 B1 | 4/2002 | Fitz | |
| 6,383,211 B1 | 5/2002 | Staehle | |
| 6,383,216 B1 | 5/2002 | Kavteladze et al. | |
| 6,391,051 B2 | 5/2002 | Sullivan, III et al. | |
| 6,425,898 B1 | 7/2002 | Wilson et al. | |
| 6,505,066 B2 | 1/2003 | Berg et al. | |
| 6,514,280 B1 | 2/2003 | Gilson | |
| 6,517,569 B2 | 2/2003 | Mikus | |
| 6,517,570 B1 | 2/2003 | Lau et al. | |
| 6,520,983 B1 | 2/2003 | Colgan et al. | |
| 6,530,947 B1 | 3/2003 | Euteneuer et al. | |
| 6,576,006 B2 | 6/2003 | Limon et al. | |
| 6,582,460 B1 | 6/2003 | Cryer | |
| 6,605,109 B2 | 8/2003 | Fiedler | |
| 6,626,934 B2 | 9/2003 | Blaeser et al. | |
| 6,641,606 B2 | 11/2003 | Ouriel et al. | |
| 6,656,212 B2 | 12/2003 | Ravenscroft et al. | |
| 6,656,213 B2 | 12/2003 | Solem | |
| 6,673,102 B1 | 1/2004 | Vonesh et al. | |
| 6,676,666 B2 | 1/2004 | Vrba et al. | |
| 6,676,693 B1 | 1/2004 | Belding et al. | |
| 6,695,862 B2 | 2/2004 | Cox et al. | |
| 6,699,274 B2 | 3/2004 | Stinson | |
| 6,726,712 B1 | 4/2004 | Raeder-Devens | |
| 6,743,219 B1 | 6/2004 | Dwyer et al. | |
| 6,773,446 B1 | 8/2004 | Dwyer et al. | |
| 2001/0034549 A1 | 10/2001 | Bartholf et al. | |
| 2003/0040789 A1 | 2/2003 | Colgan et al. | |

FOREIGN PATENT DOCUMENTS

| | | |
|---|---|---|
| EP | 0 119 688 | 9/1984 |
| EP | 0274 846 | 7/1988 |
| EP | 0 408 245 | 3/1994 |
| EP | 0 554 579 | 3/1996 |
| EP | 0 596 145 | 5/1996 |
| EP | 0 747 022 | 12/1996 |
| EP | 0 819 411 | 1/1998 |
| EP | 0 850 655 | 1/1998 |
| EP | 0 943 302 | 9/1999 |
| EP | 0 943302 A2 | 9/1999 |
| EP | 0-948 946 | 10/1999 |
| EP | 0 858 655 B1 | 2/2002 |
| EP | 0 720 837 | 6/2003 |
| WO | WO 91/07928 | 6/1991 |
| WO | WO 9515780 | 6/1995 |
| WO | WO 98/49971 | 11/1998 |
| WO | WO 99/04728 | 2/1999 |
| WO | WO 99/36119 | 7/1999 |
| WO | WO 99/44666 | 9/1999 |
| WO | WO 99/49929 | 10/1999 |
| WO | WO 0045740 | 8/2000 |
| WO | WO 00/72780 | 12/2000 |

* cited by examiner

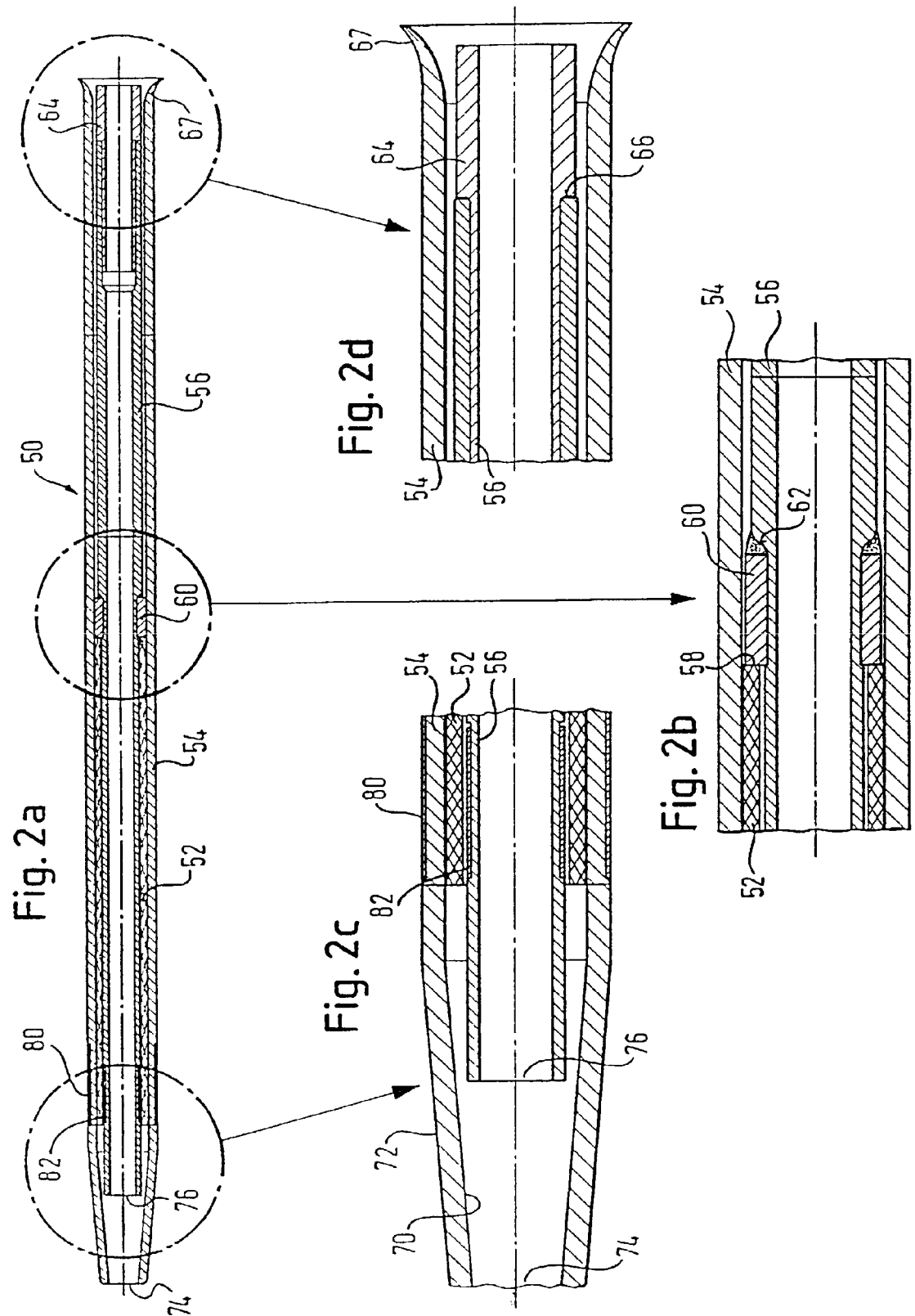

IMPLANT DELIVERY DEVICE

This application is a continuation of International Application No. PCT/EP00/11199, filed Nov. 13, 2000, which claims priority to: United Kingdom Patent Application No. 0020348.9, filed Aug. 17, 2000, German Patent Application No. 100 12 852.1, filed Mar. 16, 2000, and German Patent Application No. 199 54 330.5, filed Nov. 11, 1999. Incorporated by reference into this application is the entire disclosure of each of the above mentioned applications.

FIELD OF THE INVENTION

This invention relates to a delivery device for an implant (such as a stent) comprising a sheath having an outside surface along a length which comprises a proximal portion, a shaft portion and a distal portion, a distal end, a proximal end and a lumen which connects said ends and is adapted to receive a self-expanding implant through the proximal end and guide the implant to the distal end for deployment into a bodily lumen by expulsion from the distal end of the lumen. In a broader sense, the invention is concerned with a percutaneous, transluminal guide catheter.

BACKGROUND ART

U.S. Pat. No. 4,580,568, Gianturco discloses a stainless steel stent made of zigzag loops of stainless steel wire. Such stents have come to be known as "Z-stents". The delivery system for the Z-stent comprises a catheter with a tapered tip, fitted within a sheath. The sheath and catheter are advanced as a unit into the vascular system until the distal end of the assembly extends across the target site for stenting. Then, the taper tip catheter is withdrawn to leave the sheath in place, with its distal end extending across the stenting site. Then, an adaptor is fitted to the proximal end of the sheath to enable a compressed Z-stent to be advanced from the adaptor into the proximal end of the sheath. Then, the adaptor is removed and a polyethylene tube with a flat leading end is introduced into the proximal end of the sheath so that the leading end of the tube is in abutment with the proximal end of the Z-stent. By pushing on the tube, the Z-stent can be driven distally along the full length of the sheath until the stent resides, still within the sheath, but immediately adjacent the distal end of the sheath, and spanning the stenting site. At this point, by holding the tube against axial movement, and withdrawing the sheath proximally, the stent can be released into deployment at the stenting site, progressively, from its distal end, as the distal end of the sheath withdraws proximally through the stenting site, gradually to release the length of the stent, starting with the distal end of the length of the stent.

As the sheath withdraws proximally along the length of the stent, the stent radially expands away from the long axis of its delivery system. Because there is no structure of the delivery system within the stent envelope, so withdrawal of the delivery system, proximally away from the site of stenting, can be effected without any risk of disturbance of the stented tissue.

Above-mentioned U.S. Pat. No. 4,580,568 is a disclosure which occurred very early in the development of stent delivery systems, being based on a patent application filed in 1984. Over the last fifteen years there has been intensive development of delivery systems for self-expanding stents. For a relatively recent disclosure, reference is made to EP-A-819 411, with a priority date of 1996. The delivery system disclosed in this document confines the self-expanding stent between a bed on an inner tube and a sleeve surface on an outer tube, release of the stent being effected by proximal withdrawal of the outer sleeve. The drawings show the distal end of the delivery system abrupt and flat. In contrast, the document shows as prior art a schematic diagram of a delivery system in which a self-expanding stent is also confined in a bed between an inner tube and an outer sleeve, but the inner tube extends into an end zone, distal of the distal end of the stent, which is frusto-conical or tapered so as to provide the delivery system overall with a distal end zone which is tapered radially inwardly to its ultimate distal end face.

In both of these systems described in EP-A-819 411, the event of deployment of the stent is followed by proximal withdrawal, from within the stent envelope, of the inner tube. In both of the systems, the inner tube component of the delivery system, inside the stent envelope, has re-entrant surfaces associated with the bed in which the stent was originally confined. The present inventors have appreciated that such re-entrant surfaces are undesirable. Stents are characterised by a lattice structure in which the lattice-work openings get bigger as the radius of the stent expands during deployment. It is not inconceivable that bodily tissue within the wall of the lumen at the stenting site can protrude through lattice-work openings of the stent, into the bodily lumen, during or immediately following deployment of the stent. Then, when the inner tube is withdrawn proximally through the stented zone of the bodily lumen, any re-entrant surfaces on the inner tube distal of the proximal end of the stented zone could conceivably engage with bodily tissue inside the envelope defined by the deployed stent lattice, and this engagement could part the engaged bodily tissue from the lumen wall. Particles of tissue, once detached, could be carried away in the flow of bodily fluid within the lumen, conceivably with adverse or even fatal consequences. Therefore, the present inventors have concluded, any such re-entrant surfaces should be avoided, if at all possible.

For a recent disclosure of a stent delivery system which has no stent bed inside the stent envelope see U.S. Pat. No. 5,833,694 published Nov. 10, 1998, in which the FIG. 20 embodiment discloses a variation in which the delivery catheter has a uniform diameter and within it a pusher tube 22, the distal end 190 of which serves as a stop for the proximal end of the stent. To deploy the stent, the sheath is pulled back proximally while the distal end of the inner tube prevents proximal movement of the stent itself. A distinctive feature of the disclosure of U.S. Pat. No. 5,833,694, which distinguishes it from U.S. Pat. No 4,580,568, is its proposal to place a plurality of stent rings, one after another, by progressive proximal withdrawal steps of the sheath to release the stent rings one by one, at desired locations within the bodily lumen.

Another prior art disclosure of a stent delivery system is found in U.S. Pat. No. 5,782,855 Lau et al., in which a stent lies radially between an outer sheath and a balloon catheter. On the distal tip of the balloon catheter is a cone, into which is tucked a tapered distal tip of the outer sheath. For deployment of the stent, the sheath is withdrawn proximally with respect to the stent. After balloon expansion of the stent, the balloon catheter is withdrawn proximally so that the cone passes in the proximal direction the full length of the stent lumen. The cone has an exposed proximal-facing rim edge as is passes through the stent lumen.

U.S. Pat. No. 6,019,778 Cordis Corporation discloses a delivery apparatus for a self-expanding shape memory alloy stent which features a stent bed on an inner shaft and an outer sheath which includes a braided reinforcing layer. There is a stop on the shaft member, proximal of the stent bed, to prevent proximal movement of the stent when the outer sheath is withdrawn proximally to release the stent. The braided reinforcement layer is preferably made from stainless steel and is said to resist a tendency of the stent to become imbedded within the sheath which surrounds it.

EP-A-720 837 Fischell discloses an integrated double-function catheter system for balloon angioplasty and stent delivery. An outer sheath with a conically-shaped distal tip portion surrounds a stent. Radially inside the stent is a balloon catheter. The balloon is located well distal of the stent so as to allow better trackability of the distal end of the catheter over a flexible guidewire and through tortuous coronary arteries and through a long tight stenosis. The provision of the conically-shaped distal portion of the outer sheath is said to enable proper placement of the stent, even in cases of severe intimal dissection which could cause an intimal flap that could block the passage of an outer sheath having a blunt end.

EP-A-554 579 discloses a stent delivery device with coaxial shaft and sheath for a self-expanding stent. The sheath is provided at its distal tip with a protective tip which is bonded to the sheath thermally or with adhesive, or can be made integral with the sheath. This tip is said to reduce the likelihood of injury to the bodily lumen wall during advancement of the catheter in the lumen.

EP-A-119 688 Balco published September 1984 discloses a process and apparatus for restoring patency to bodily vessels in which a shape memory alloy wire is contained within an outer sheath and is abutted at its proximal end by a pushing shaft. It is deployed by withdrawing the sheath proximally. The diameter of the sheath surrounding the prosthesis is very much greater than the diameter of the sheath for the remainder of its transluminal length, over which it is a relatively snug fit with the pushing shaft. The sheath is said to be inserted, as by conventional techniques, into the aorta of the patient, in order that the prosthesis can be placed at an aneurysm.

U.S. Pat. No. 4,665,918 is another example of disclosure of a delivery system for a self-expanding stent held within a surrounding sleeve which is proximally withdrawn relative to a stent bed in a coaxial inner shaft, and with a tapered tip zone on the shaft which protrudes beyond the distal end of the surrounding sleeve.

U.S. Pat. No. 5,662,703 discloses a delivery device for a self-expanding stent, having an outer catheter surrounding an inner catheter and a tubular stent-retaining sheath formed of a rolling membrane. The self-expanding stent is located at the distal ends of the inner and outer catheters. The stent is radially inwardly constrained by a double-walled rollable membrane. The separate proximal ends of the radially inner and outer membrane portions are fixed respectively to inner and outer catheter components whereas the contiguous-distal ends of the membrane portions converge and narrow thereby to form a tapered tip. For stent release, the outer catheter is moved proximally at least twice the length of the stent in order to pull back proximally both the inner and outer layers of the membrane, thereby releasing the stent.

U.S. Pat. No. 5,735,859 discloses a stent delivery device comprising an inner and outer catheter and a stent covered by a thin-walled sheath. The inner catheter projects beyond the distal end of is fixed to the distal end of the outer catheter. The distal end of the sheath is releasably received in the distal section of the inner catheter distal to the stent. The sheath can be released from the distal section of the inner catheter and pulled back from the stent, thereby releasing said stent. The stent can either be self-expandable or expanded by a balloon. Where the distal end of the sheath is received in the distal section of the inner catheter, a step in the radially outside surface of the inner catheter is present.

EP-A-747 022 discloses a coil-reinforced retractable sleeve for a stent delivery catheter. One embodiment of the sleeve has a distal tip which tapers inwardly and is provided with a plurality of slits which extend proximally from the distal end of the sleeve and substantially parallel to the longitudinal axis of the sleeve, the slits functioning to provide the sleeve with a low profile adapted for traveling through a blood vessel.

EP-A-948 946 discloses apparatus and methods for deployment and release of an intraluminal graft for treating a stenosis, the graft being surrounded by a cylindrical cover which is withdrawn proximally to release the graft. The cover can have an atraumatic distal end of reduced diameter in which there are slits extending axially from the distal end wall.

WO 99/49929 discloses a rapid exchange delivery system for stenting a body lumen, with the stent being covered by a retractable sheath, and the stent itself being mounted on a balloon. In the drawings, it appears that the diameter of the sheath is somewhat greater radially outside the stent than in a distal end zone of the sheath, distal of the stent, touching the underlying balloon.

EP-A-850 655 discloses a catheter tip mold and cut process in which the molding process creates flash which extends beyond the desired catheter tip, which flash is then parted from the distal end of the molded catheter tip by use of a cutter. U.S. Pat. No. 5,843,090 is another disclosure of an inner catheter with a step at its distal end (see FIG. 6) when the outer catheter is withdrawn proximally. See also U.S. Pat. No. 5,743,874 for a further disclosure of an inner catheter with a step (FIG. 1, feature 81) in its outer surface.

Incorporated by reference are all the disclosures of all the above mentioned prior publications.

SUMMARY

It is one object of the present invention to provide a system for delivering self-expanding stents to stenting sites within the body, which minimises trauma to the affected tissue of the patient yet, at the same time, offers the medical practitioner a robust and simple system for stent placement.

It is another object of the present invention to mitigate these disadvantages of the previously proposed stent delivery systems.

According to one aspect of the invention, there is provided a stent guide catheter, which has a radially outwardly exposed surface radially inwardly tapered surface adjacent the distal end of the sheath, said surface being provided by a tapered tip to the sheath.

Thus, unlike previously proposed systems in which a tapered tip of the delivery system is provided by the inner tube, that is, the structure radially inside the stent, the present invention proposes that the tapered tip shall be provided on a catheter which receives the stent as its proximal end, constrains the stent against radially-outward expansion, and accepts axial advance of the stent along its lumen to its distal end. A device which advances the stent in this way can also serve as a stent pusher, to maintain the position of the stent relative to a stenosis, as the guide catheter is withdrawn proximally.

Furthermore, the present invention opens up possibilities to avoid any surfaces on the radially outside surface of the delivery system which have the potential to come into contact with the tissue of the bodily lumen, in the zone of the lumen to be stented, prior to deployment of the stent. Before the stent can be deployed, the distal end of the delivery system has to be advanced through the zone to be stented. If that distal end includes surfaces which could engage bodily lumen wall tissue and cause it to detach from the wall, or at least weaken the connection between it and the lumen wall then, again, there is a risk of detachment of bodily tissue, and adverse consequences.

A sheath with a tapered distal tip has already been described by the present applicant in German patent applications DE 19954330.5 filed Nov. 11, 1999 and DE 10012852.1 filed Mar. 16, 2000. The content of these two already filed German patent applications is incorporated herein by reference. Additionally, disclosure from the description and drawings of each of the two German patent applications is included, in English translation, in the text below.

In another aspect, the present invention provides a sheath which is, at the same time, both a guide catheter and an outer sheath for a delivery system for a self-expanding implant (such as a stent).

Conventionally, stent delivery systems are used in conjunction with a previously deployed guide catheter. Thus, at a point of entry into the body of the patient, a catheter introducer is inserted. With the catheter introducer in place, a guide catheter can be advanced through the introducer and along the designated bodily lumen of the patient until the distal end of the guide catheter is at the desired site relative to the target site for stenting. The guide catheter can be used as a channel for advancement and withdrawal of whatever further devices are prescribed by the treatment, until such time as the stent placing step is to be carried out, at which point the stent delivery system is advanced distally along within the lumen of the guide catheter.

It is of course a disadvantage of such procedures that the maximum outside diameter of the stent delivery system must be smaller than the inside diameter of the guide catheter tube. However, in the present invention, it is the tube of the guide catheter which can be used as the outer sheath of the actual delivery system for the stent so that, for a given outside diameter of guide catheter, relatively larger stents can be selected. Alternatively, for any particular diameter of stent, the delivery system outside diameter can be reduced, for the present invention, in comparison with conventional technology.

Conventionally, guide catheters are often figurated, that is to say, a distal portion of the length of the catheter shaft is pre-configured in a non-linear shape such as a J-shape, the shape being carefully specified to correspond to the desired route through the lumen geography which the distal end of the guide catheter is required to navigate, in order to make possible, or facilitate, the task of the medical practitioner in guiding the distal end of the guide catheter to the desired location within the body of the patient. Accordingly, it is envisaged that particular embodiments of the implant delivery device of the present invention will feature a sheath having a figurated distal length portion.

Although stent technology has been driven forward rapidly by the demands of cardiac surgery, stents are becoming more ubiquitous, and are increasingly being specified for peripheral arterial procedures, as well as for such other applications as lumens of the urological system, and for the biliary tract. The present invention has application to all of these procedures.

However, a procedure where the technical effects offered by the present invention are particularly attractive is the procedure of stenting the carotid artery. This is because the artery lies so close to the brain, so that detachment of any bodily tissue, at the stenting site, is liable to be carried by the blood flow into the brain of the patient, which is of course not wanted. Accordingly, in a stenting procedure for the carotid artery, a preliminary procedural step is the placement of a protection device between the site of stenting and the brain so that any particulate material dislodged at the stenting site will be prevented by the device from proceeding further along in the carotid artery. With the sheath of the present invention, the distal end zone is devoid of any discontinuities, having only an unbroken smoothly tapered outside surface, so is less likely than any other system to dislodge material from the wall of the carotid artery as the distal end zone of the sheath is advanced past the target site of stenting.

Furthermore, during deployment of the stent, as the outer sheath is withdrawn proximally, again there are no discontinuities in the surface which could conceivably snag on tissue surfaces in the artery wall.

As with above-mentioned U.S. Pat. No. 5,833,694, the system could deliver a sequence of implants, by stepwise proximal withdrawal of the outer sheath, to release the implants, one-by-one, into their desired locations within the bodily lumen.

Further, once the outer sheath has been withdrawn to a position proximal of the stented zone, there is no remaining inner tube to withdraw through the stented zone. The protection device, on the other side of the stented zone, has still to be withdrawn through the stent lumen, but details of protection devices and their withdrawal procedures is not part of the present invention. Note that axial movement of the outer sheath, before after deployment of the or each implant, need not be accompanied by any axial movement of any extension of any inner shaft member beyond the distal end of the outer sheath.

Trans-luminal stenting procedures presently rely heavily on radiological visualisation techniques. In one particular embodiment of the present invention, the tapered tip of the sheath is, to start with closed or substantially closed, such as by a membrane which can be ruptured later in the procedure, as required. This allows the sheath to be filled with radiological fluid, for enhanced visualisation of the distal end zone of the sheath. The radiological fluid is present at the end zone continuously, while the tip is closed, and the radiological fluid is not being diluted by the flow of bodily fluids through the lumen. After the distal end zone of the sheath has been brought to the desired location, at the zone of stenting, then the closed end of the sheath can be broken, either by advancement of a guidewire through the closed end, or by proximal withdrawal of the sheath over the stent itself, during deployment of the stent.

Even with a sheath of the present invention with a distal end which is open from the outset, a snug fit over a guidewire represents a more or less closed distal end of the sheath, thereby allowing a substantial improvement in radiological visualisation of the position of the distal end zone of the sheath, relative to conventional guide catheters.

The material of the outer catheter and the deformable tip is a thermoplastic polymer, which is steplessly extruded as a pre-form in a an extrusion process, known per se, to form a sleeve for the inner catheter and a cavity for the stent. Preferably, the final shape of the tip is defined in a subsequent shaping operation. In one preferred embodiment a mandrel is inserted in the sleeve from the proximal to the distal end. Then the tip, with the mandrel inside it, is inserted into a hollow mould. Hereafter, the pre-form is heated in the hollow mould to a temperature for plastic deformation. The plastic material is pressed against the inner walls of the mould by advancing the mandrel, whereby the final shape of the tip is formed. The tip is thereby provided with blunt, e.g. rounded, edges. The catheter system according to the invention is particularly advantageous since the outer diameter of the sleeve runs into the flexible tip without a step, gap or edge, and because the tip and sleeve are contiguous and unitary.

The flexible soft tip ensures insertion and easy guidance of the stent delivery catheter systems as well as atraumatic advance and withdrawal in the patient's body. Depending on the use, the tip may have different shapes, such as conical. It may be used with or without a guide wire fed through a bore in the tip and all along a lumen of the inner catheter. The shape and composition of the tip can be selected to ensure good penetration of, for example, a stenosis. The location of the distal end of the catheter system from outside the body can be checked, as is known, by means of a suitable radiopaque marker.

In addition, or as an alternative, the catheter lumen can be used to deliver a contrast liquid supplied at the proximal end of the catheter system and delivered all the way up to the tip, thereby locating the stenosis. The same system can be used to transport a rinsing liquid to the tip region. By establishing a reduced pressure at a port connected to the proximal end of said delivery system a vacuum can be created in the tip region, which is useful for, for example, sucking away contrast or bodily fluids. Once the catheter's distal end is brought to the desired location, markers affixed to, or part of, the inner catheter and/or the stent to reveal the positions of at least one of the distal and proximal end of the stent can be used to fine tune the position of the self-expanding stent relative to the stenosis. For stent placement, the inner catheter carrying the self-expanding stent is kept in the same position while pulling the tip, via the outer catheter, proximally onto and along the stent length.

While the now uncovered distal end of the stent expands, a radially inward reaction force exerted by the sleeve and tip onto the stent keeps the proximal remainder of the stent length radially inwardly constrained, and prevents premature release.

Upon retraction of the tip beyond the proximal end of the stent, to complete the release, the stent is fully free to expand away from the delivery system. The distal end of the inner catheter can then be moved proximally, to bring it inside the outer catheter. Then, the whole catheter system can be withdrawn from the vessel. Since no edge, gap or step exists, where the tip and outer catheter merge, pulling the catheter rearwardly out of the body will not traumatize tissue over which the catheter slides.

If desired, the inner catheter can be completely removed while the outer catheter remains in the body. It can now be considered whether to reload the inner catheter with a stent, or to insert a fresh inner catheter carrying a stent of the same or different size into the outer catheter. The distal part of the catheter system can be moved to a new position in order to place a second stent. As an alternative, one may use the empty outer catheter as a multi-purpose tool for bringing other fluids or devices to the same or another desired location in the body.

The wall thickness of the tip may be kept constant, in which case the clearance between the inner surface of the mold and the mandrel has to be constant during the tip-shaping operation. Alternatively it may vary, e.g. continuously or discontinuously decline from the proximal to the distal end.

Depending on the stent size the tip may be heterogeneous, i.e. zones of different hardness or zones of different composition. Especially in the case of large diameter stents, the tip may have at least one stretch zone such as an axially oriented zone of reduced resistance to radially outward deformation (tear zones), i.e. a slit, a reduction in wall thickness or strips of reduced resistance, to facilitate expansion of the tip over the distal end of the stent.

For a better understanding of the present invention, and to show more clearly how the same may be carried into effect, a reference will now be made, by way of example, to the accompanying drawings.

BRIEF DESCRIPTION OF THE DRAWINGS

FIGS. 1a to j present a sequence of steps for stenting a stenosis in the carotid artery, each diagram taking the form of a diametral section through the aortic arch and common, internal and external carotid artery (CCA, ICA, ECA) and stenosed site in the right ICA;

FIG. 2a is a longitudinal diametral section through a catheter delivery device for a biliary stent;

FIGS. 2b, c and d are portions of FIG. 2a at an enlarged scale;

DETAILED DESCRIPTION

Figure 1A:
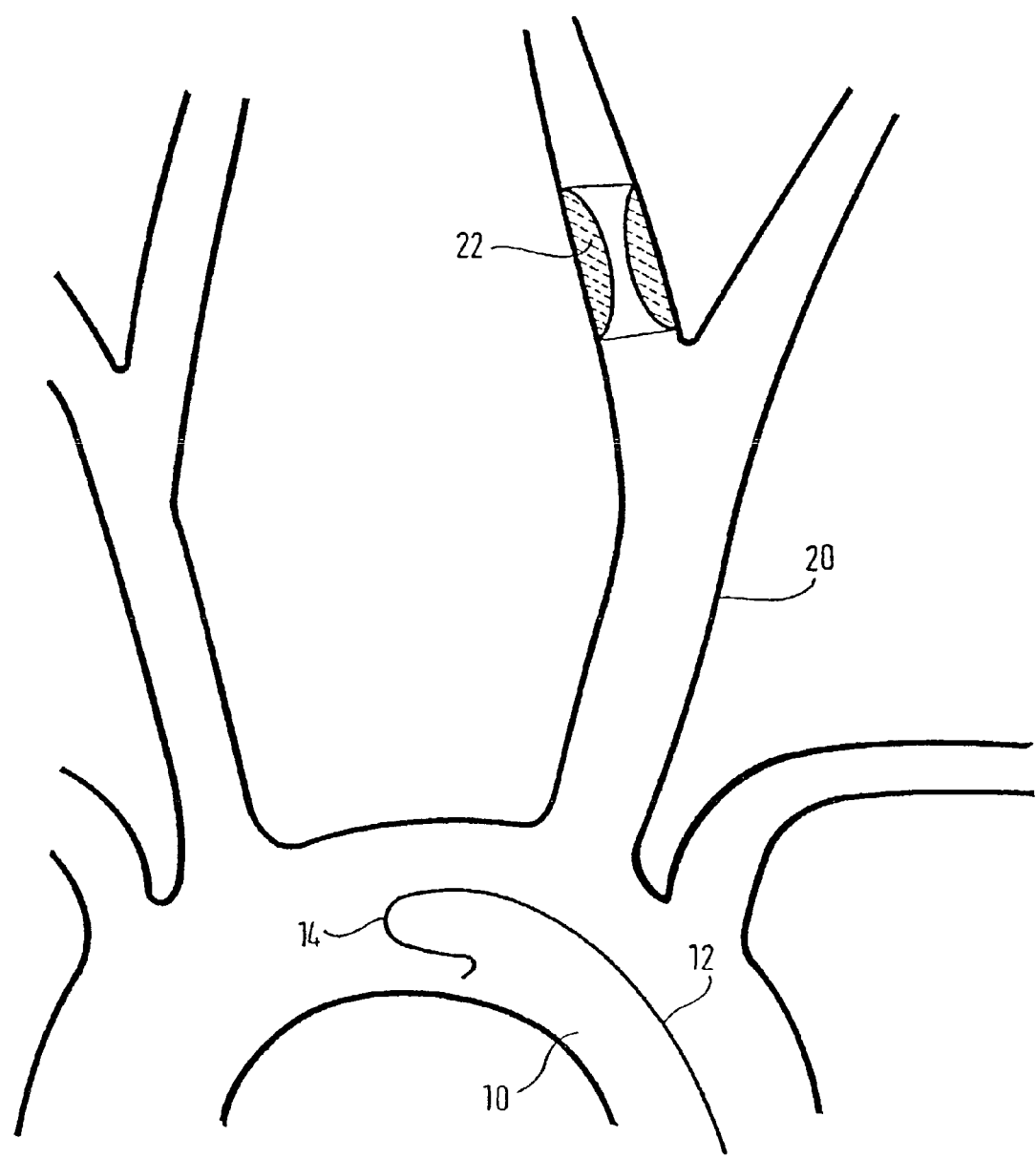
Figure 1B:
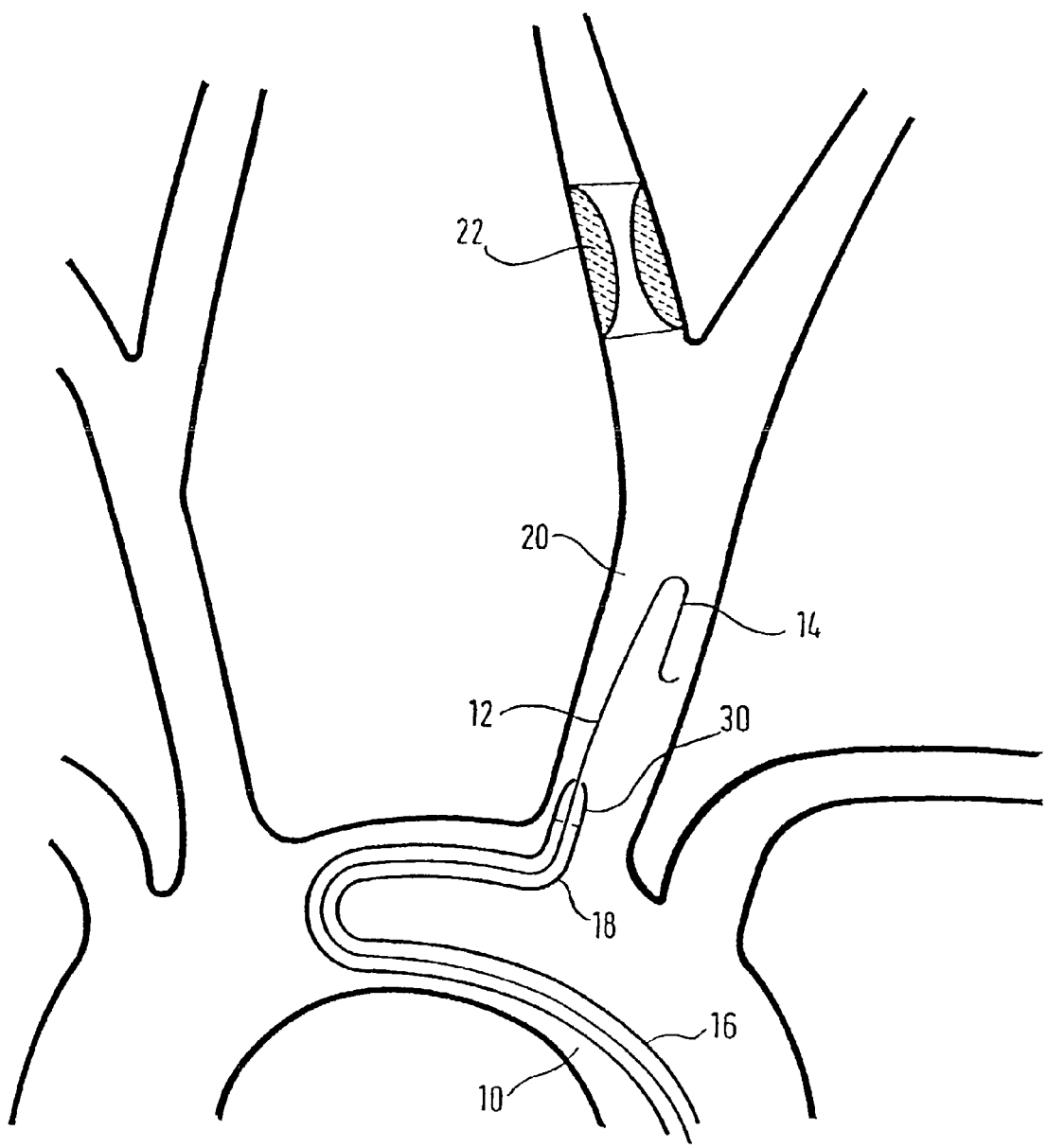

Referring first to FIG. 1a, there is shown in the aortic arch 10 a guidewire 12 with a configured tip portion 14. In FIG. 1b a catheter 16, with a figurated tip portion 18 of its length, has been advanced along the guidewire 12 and the guidewire and catheter have been manipulated to bring them into the right carotid artery (CA) 20. The catheter has a tapered tip 30 and is a stent delivery device in accordance with the present invention.

Figure 1C:
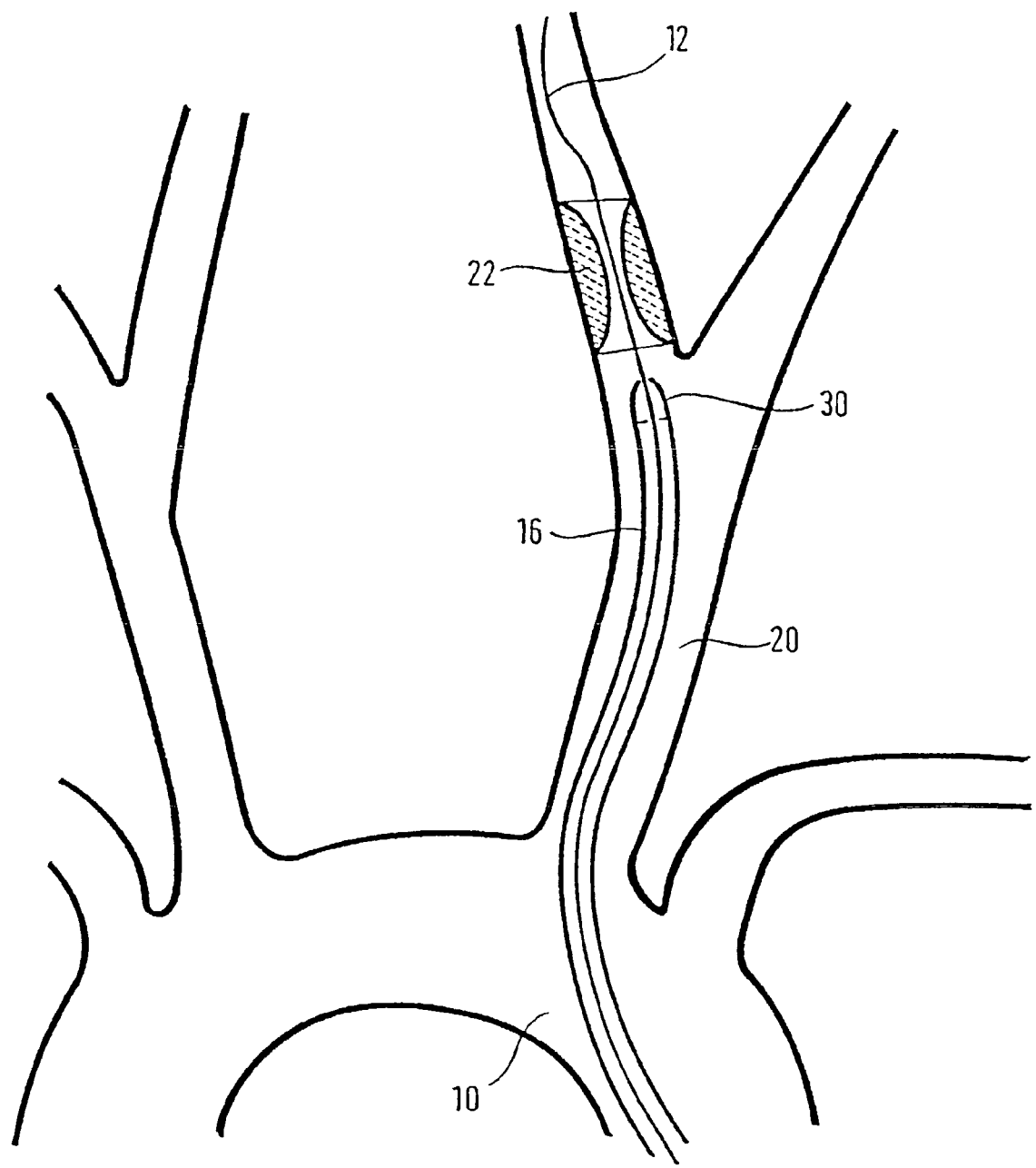
Figure 1D:
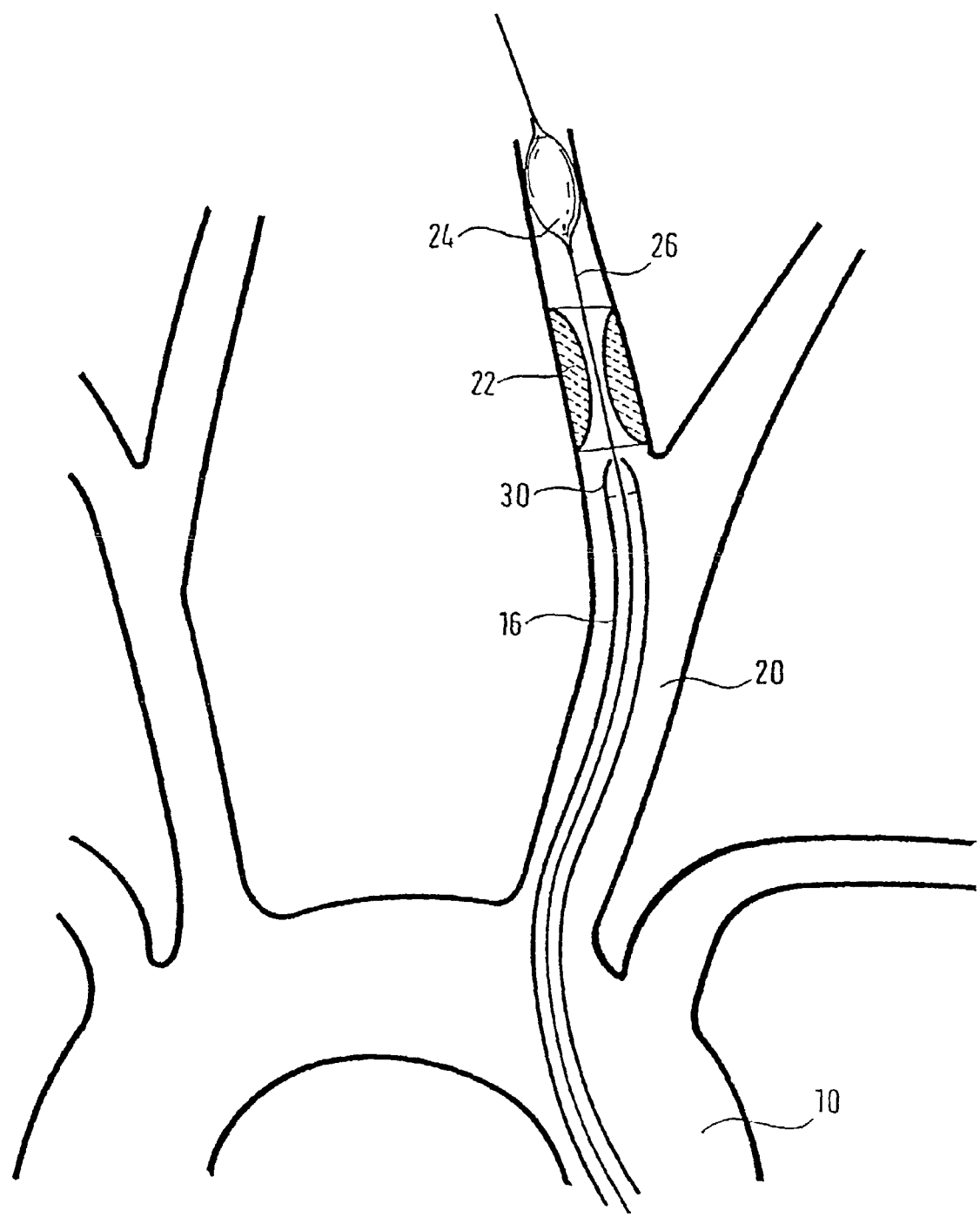

In FIG. 1c, we see that the guidewire 12 and catheter 16 have been advanced past the bifurcation of the right external (ECA) and internal (ICA) carotid artery so that the tip 30 of the catheter 16 is facing the target stenosis 22 in the right ICA. The guidewire 12 has been advanced through the stenosis. With the catheter 16 addressing the stenosis 22, the guidewire 12 is withdrawn completely and the catheter 16 is used to guide a protection device 24 into position. In FIG. 1d, there is shown the protection device 24 in the form of a balloon carried on an inflation lumen 26. By pushing on the inflation lumen 26, the protection device 24 can be advanced from the proximal end of the catheter 16, through the entire length of the catheter and its tapered tip 30, and through the stenosis 22, to arrive at the location shown in FIG. 1d. By advancing inflation fluid through the inflation lumen, the protection device balloon 24 is inflated, thereby to occlude the right ICA and prevent entrainment in the arterial flow of any detritus dislodged from the stenosis 22.

Figure 1E:
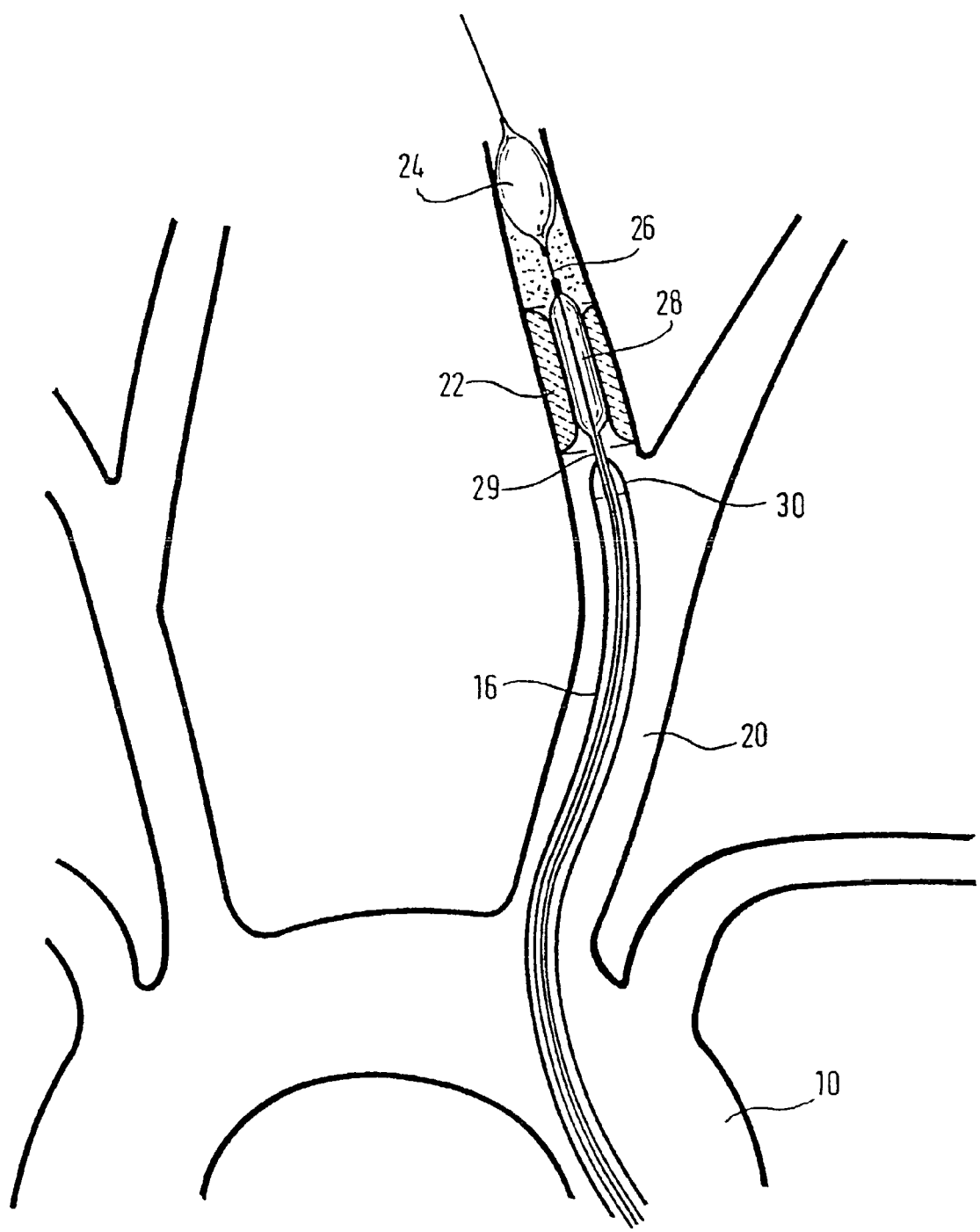

Turning now to FIG. 1e, this diagram shows that a pre-dilatation balloon 28 has been advanced, by pushing on its inflation lumen 29, which itself runs over the tube which defines the inflation lumen 26 of the protection device 24, through the full length of the catheter 16 and its tip 30, and into place, within the stenosed region 22 of the artery. The pre-dilatation balloon 28 can then be inflated, to prepare the stenosis for stenting by stretching and pre-dilating it. Any detritus or plaque dislodged during this pre-dilatation step is confined by the protection device 24 and prevented from migrating in arterial blood towards the brain.

After this pre-dilatation, the balloon 28 is deflated and, in this condition, can be withdrawn proximally into the catheter 16, notwithstanding its tapered distal end 30. Current balloon design can achieve passing diameters for deflated balloons which are significantly smaller than in the past, and small enough easily to pass through the axial distal opening of the tapered tip 30 of the catheter devices described in this patent application. With the pre-dilatation balloon device removed from the system, but with the positions of the catheter 16 and protection device 24 unchanged, a stent 32 is introduced into the axial proximal end opening of the catheter 16. Conveniently, the stent is a self-expanding stent, held confined within a lumen of a loading device (not shown) which is offered up to the proximal end of the catheter in end to end abutment. With an elongate pusher which is longer than the catheter 16, the stent is advanced from the loading device into the proximal end of the catheter lumen and then, with further pushing, through the full shaft length of the catheter to bring it to the distal tip portion 18 of the catheter shaft length.

Figure 1F:
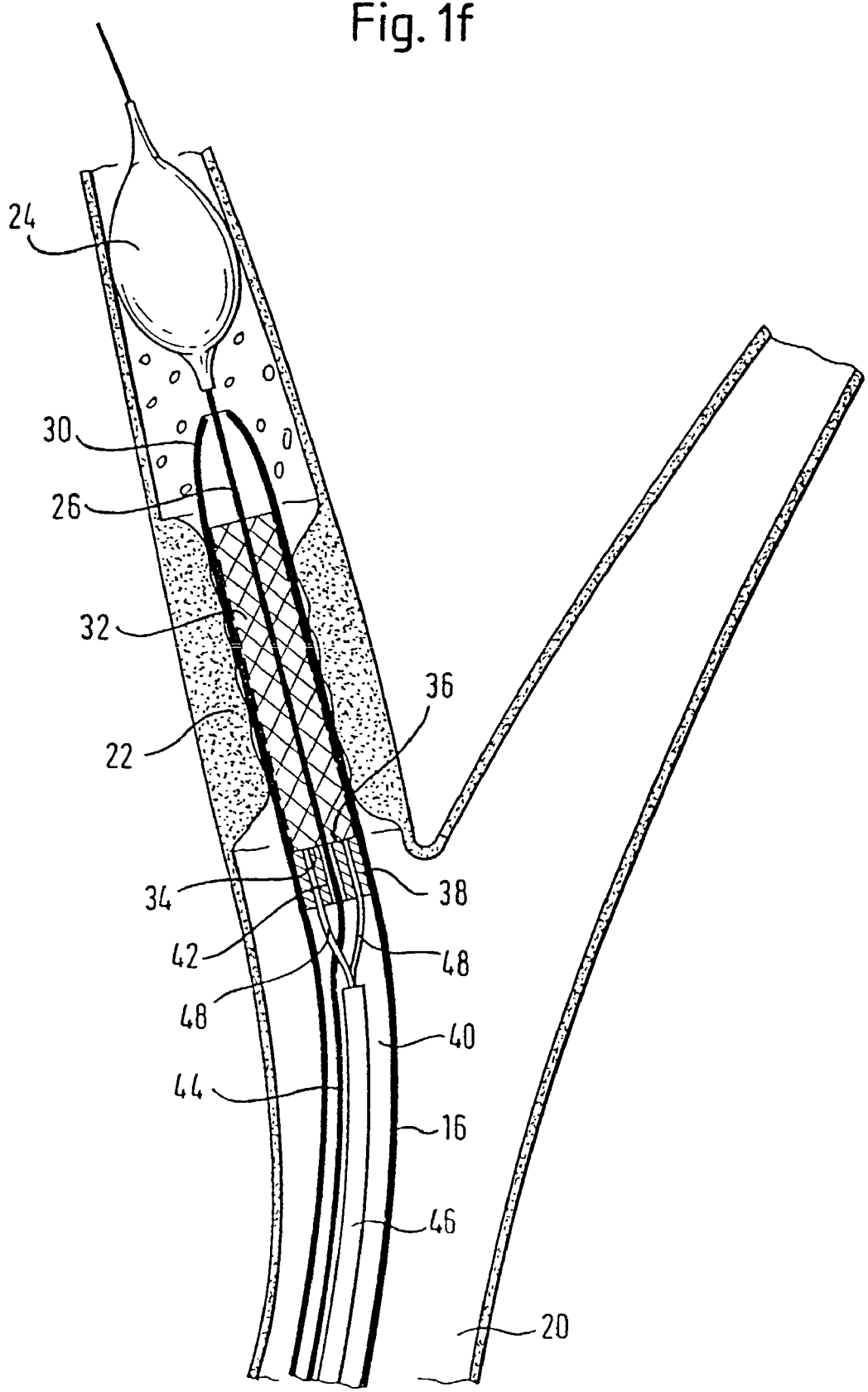

Now, to deploy the stent out of the catheter into the stenosis, the procedure shown in FIG. 1f is followed.

In FIG. 1f, the catheter 16 carries near its distal tip 30 the compressed self-expanding stent 32. The stent 32 has a proximal end surface 34 against which abuts a distal-facing end surface 36 of a pusher block 38 which fits snugly within the lumen 40 of the catheter 16 On the axis of the pusher block 38 is a bore 42 through which passes the tube 44 which defines the inflation lumen 26 of the protection device 24. This tube 44 runs through the catheter lumen 40 and parallel with a pushing wire 46 which is connected to the pusher block 38 by a pair of push links 48. In this way, the push rod 46 can take up a position co-linear with the axis of the lumen 40 and the axial bore 42 in the pusher block 38.

Comparing FIG. 1e with FIG. 1f, it will be noted that the distal tip 30 of the catheter 16 has, at this point in the procedure, been advanced through the lesion of the stenosis 22. This puts the stent 32 in the desired axial position relative to the lesion 22. For deployment of the stent, the catheter 16 is withdrawn proximally while at the same time the pusher rod 46 is held against proximal movement so that the pusher block 38 prevents any proximal movement of the stent 32 during proximal withdrawal of the catheter 16 surrounding the stent. It will be appreciated that the tapered proximal tip 30 of the catheter will grip the outside cylindrical surface of the stent as it is withdrawn proximally over the length of the stent. This gripping action will help to restrain any tendency of the self-expanding stent, as it emerges from the distal end aperture of the catheter, from urging itself distally away from the reference position defined by the distal surface 36 of the pusher block 38.

Figure 1G:
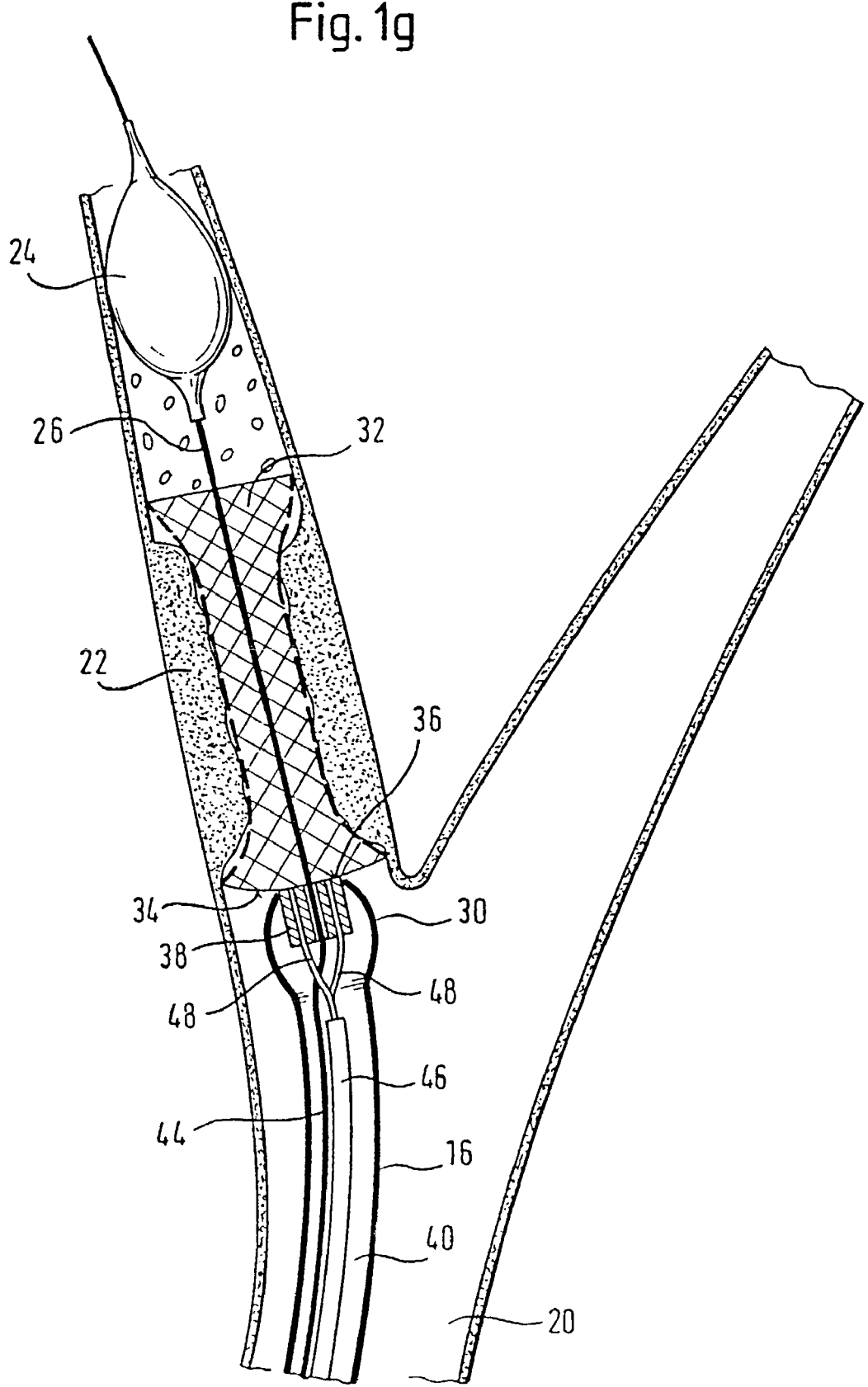

Turning now to FIG. 1g, this shows the situation at the moment of final release of the proximal-most part of the stent length from the distal-axial opening of the catheter 16, so that the distal catheter opening is fitting snugly around the distal end face of the pusher block 38. The stent is fully deployed within the lesion 22, and the protection device is still in place and confining detritus released by the stenting operation. The pushing wire 46 and pusher block 38 can then be withdrawn proximally, completely out of the catheter 16.

Figure 1H:
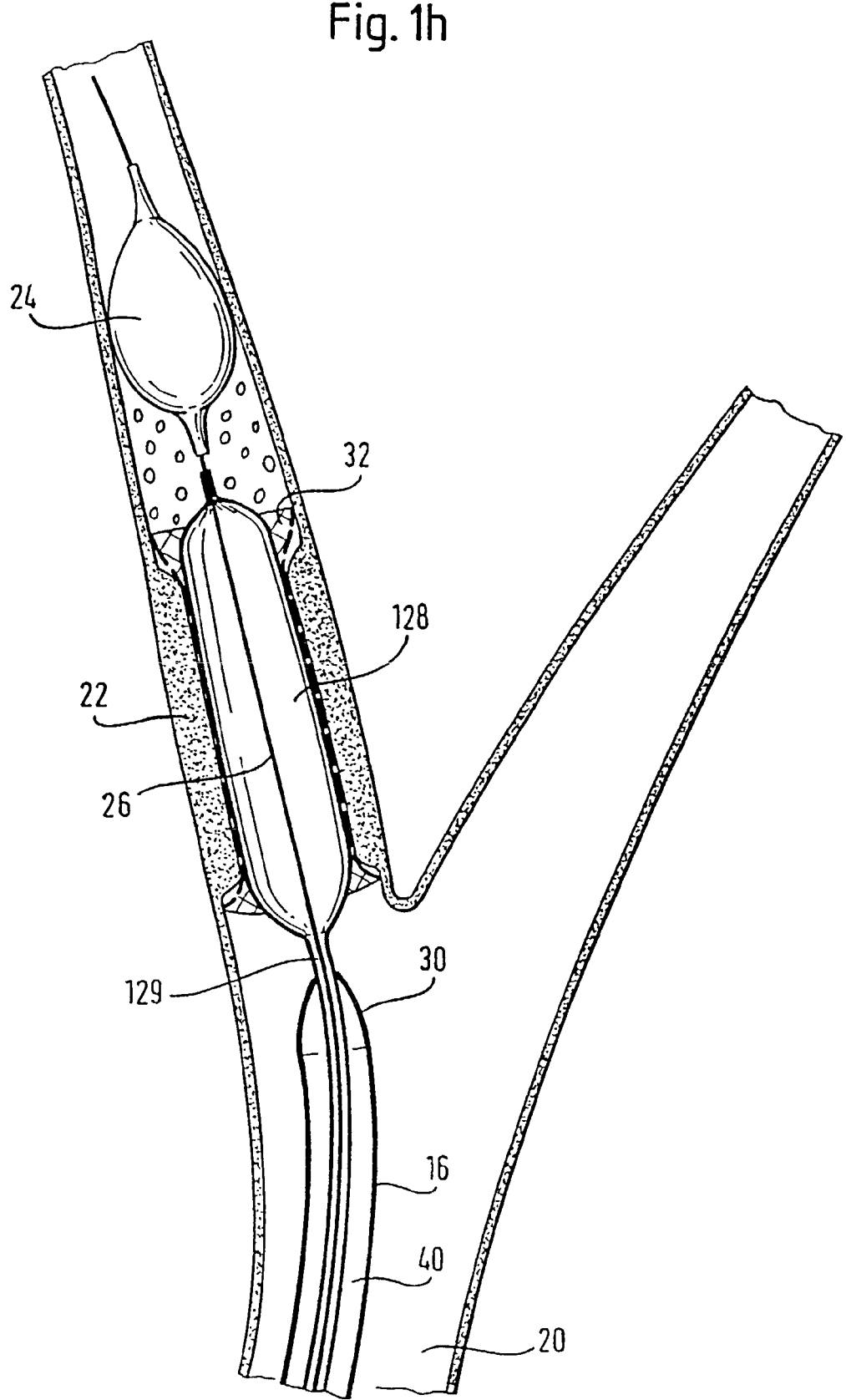

If desired, post-stenting balloon dilatation can be carried out, as shown in FIG. 1h, and by steps analogous to those described above in relation to pre-dilatation. A post-dilatation balloon 128 is advanced into position by advancing it and its inflation lumen 129 over the inflation lumen 26 of the protection device.

Figure 1J:
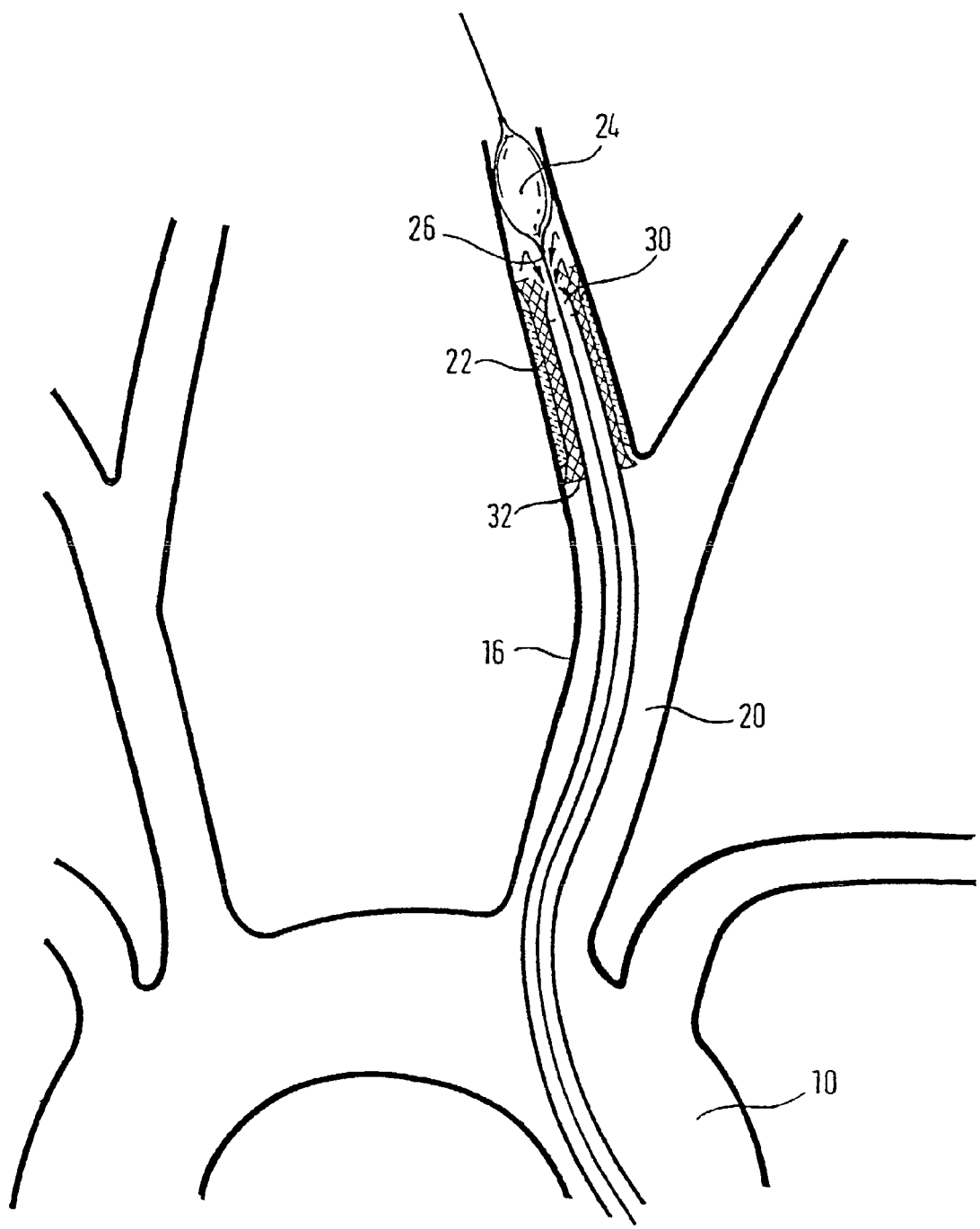

After serving in all the stenting operations up to this point, the same catheter 16 can be employed for aspiration. Referring to FIG. 1j, the catheter 16 has been advanced distally into and through the stented stenosis 22 up to a position closely adjacent the balloon 24 of the protection device. Simply by imposing a pressure differential on the lumen of the catheter 16, detritus and fluid in the stenosed region, up to the balloon of the protection device, can be aspirated into the lumen of the catheter 16, to ensure that no loose detritus remains in the stenosed artery. Once satisfactory aspiration has been achieved, then the protection device balloon can be deflated and withdrawn proximally into the catheter lumen and then the catheter/protection device assembly can be withdrawn from the body.

Those skilled in the art will be familiar with radiographic techniques for tracking the progress of devices in the body, and with choice of materials and assembly techniques for building stent delivery systems which are visible radiographically and have the required flexibility, pushability, and small transverse dimensions. For the FIG. 1 embodiment, we have described process steps rather more than constructional details of the delivery system. However, for our second embodiment, for placement of biliary stent, we will describe more of the construction of the catheter system. Those skilled in the art will find this description of constructional details useful also in connection with the FIG. 1 device for the carotid artery.

Thus, referring now to FIG. 2 there is shown a biliary stent delivery device 50 for delivery of a stent 52 to the bile duct, this stent being preferably a self-expanding stent of Nitinol shape memory alloy confined within the lumen of an outer sheath 54 and lying radially outside the tubular wall of an inner shaft 56 of the delivery device 50. For deployment of the stent, the distal end of the delivery device is arranged so that the confined stent 52 lies inside the stenosed region to be treated and then, holding the inner shaft 56 against proximal movement, the outer sheath 54 is withdrawn proximally, so as to release the stent into the stenosed region.

The stent is preferably a MEMOTHERM® stent, available from the present Applicant, but other stent designs from other manufacturers are also amenable to delivery by the devices of the present invention.

The stent 52 has a proximal end 58 which is more clearly visible in FIG. 2b. This proximal end abuts in end-to-end relationship the distal end surface of a platinum-iridium radiopaque marker band 60. This band 60 is fixed at a step 62 in the radial wall thickness of the inner shaft 56. Proximal of the marker band 60 the shaft wall thickness is relatively large and within the wall thickness is provided a braiding reinforcement of stainless steel wire having a diameter of 0.05 mm at a density of 45 crossings per linear inch of the shaft length (17.5 crossings per linear centimeter of the shaft length).

Distal of the step, the thickness of the wall of the inner shaft is smaller but the shaft is made of the same synthetic polymeric material, namely PEBAX 7233, which is an amide-based thermoplastic elastomer available from Elf Atochem of France.

At the proximal end of the inner shaft 56, the shaft receives the distal tip of a metal pusher rod 64 which is controlled from a handpiece (not shown) of the delivery device. During deployment of the stent, the inner shaft is in lengthwise compression. FIG. 2*d* shows more clearly how the proximal end of the shaft 56 abuts a step 66 in the metal push rod 64, for transferring compression stress between the rod 64 and the shaft 66.

Turning now to the outer sheath 54, this is formed in its distal part from PEBAX 4033 polymer (Elf Atochem) but in a proximal portion of its length from a polyamide Nylon (DuPont trade mark) resin which is reinforced by braiding of the same description as that which reinforces the inner shaft. The transition from PEBAX 4033 to Nylon is accomplished in three steps, namely from PEBAX 4033 to PEBAX 6333, then to PEBAX 7233, and thereafter to Nylon. The overall length of the outer sheath is around 190 cm, of which only the distalmost 25 cms is of PEBAX 4033. This distal portion of the length of the outer sheath is colourless and translucent, but the parts of the sheath proximal thereof are coloured blue and are opaque. Likewise, the inner shaft is blue opaque in all portions proximal of the radiopaque marker band 60. The stent itself is 11 cms long.

At its proximal end, the Nylon outer sheath is provided with an outward flare 67 to enable it to be clamped into a coaxial threaded boss on the handpiece control unit at the proximal end of the device.

At the distal end of the outer sheath 54 is a tapered tip which is molded out of the material of the wall of the sheath, in a manner known per se and as described in more detail in our above-mentioned co-pending German patent application No. 10012852. The tip has parallel luminal 70 and abluminal 72 wall surfaces and a constant wall thickness all the way to the distal opening 74 of the tip, which has a diameter which is approximately the same as the diameter of the distal opening 76 of the inner shaft. Not visible in the drawings are two lengthwise slits in the wall thickness of the outer sheath, running from the distal opening 74 proximally back over most of the length of the tapered tip and arranged diametrically opposite each other on the tip. These slits reduce the tensile stress needed to pull the outer sheath proximally back over the stent length during stent deployment.

In a variation, the wall thickness of the tapered distal tip of the outer sheath could be progressively reduced towards the final distal opening 74, in order to accommodate the deformation of the tip during stent deployment as elastic deformation of the distal end of the distal tip, rather than by the use of slits.

Swaged onto the shaft of the outer sheath 54, just proximal of its tapered tip, and on its radially outside surface, is a platinum-iridium marker band 80 which serves to indicate by its radiopacity the location of the distal end of the outer sheath in the body. Radially inside this marker band 80 is a similar platinum-iridium marker band 82 swaged to the radially outside surface of the inner shaft 56, just proximal of its distal end opening 76. In fact, the distal end of the radiopaque marker 82 corresponds in its axial location on the inner shaft 56 with the distal end of the compressed stent 52. As can be seen from the figures, when the inner shaft 56 and outer sheath 54 are in their respective axial positions appropriate for commencement of deployment of the sheath 52, then the two marker bands 80 and 82 lie radially one inside the other so that the radiographer sees only two radiopaque bands with one of these indicating the distal end of the stent and the other indicating the proximal end of the stent. Once stent deployment commences, and there is relative proximal movement of marker band 80 relative to band 82, then the radiographer will see a region of opacity corresponding to band 80 progressively moving away from band 82 and towards band 60. When this region of opacity is significantly proximal of band 60, this will indicate that the stent has been fully released from the delivery system.

At this point, the distal end opening 74 of the outer sheath 54 will lie proximal of the stented stenosis but the inner shaft 56, for the whole of its length distal of the marker band 60, will lie distal of the end opening 74 of the outer shaft. Retraction of this distal end zone of the inner shaft into the lumen of the outer sheath is straightforward, however, because there are no re-entrant surfaces on the inner shaft distal of the marker band, so this portion can readily be drawn proximally through the stent lumen without snagging on any bodily tissue which might be protruding into the stent lumen through the open lattice-work of the expanded stent.

The skilled reader will appreciate that the single stent could instead be two or more stents arranged in abutting end-to-end relationship as in above-mentioned U.S. Pat. No. 5,833,694, and will appreciate what manipulations of the delivery system will serve to deploy the implant elements successively, one by one.

It is to be noted that there is great simplicity in the structure contained within the outer sheath 54. This simple structure, in combination with a stent which can be compressed to small dimensions, allows the building of systems with notably small passing diameters.

Figure 3:
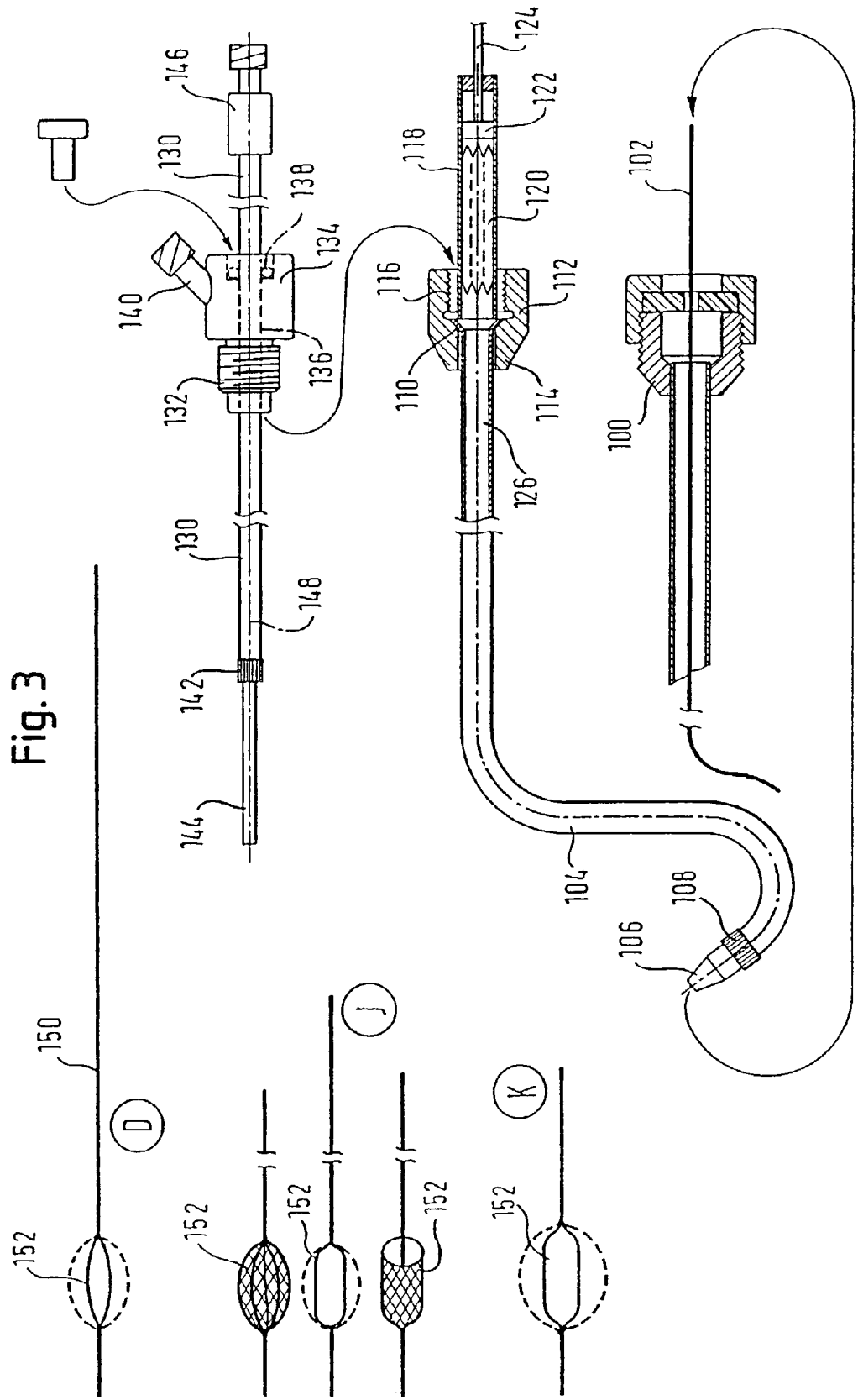
FIG. 3 is a view from the side of the components of a procedure kit which includes a delivery device in accordance with FIG. 1.

Turning now to drawing FIG. 3, there is shown various elements forming a procedure kit for delivery of a stent to the carotid artery. The skilled reader will recognise a number of the elements of this kit and will therefore be able to put in the context of these familiar elements the novel elements of the present invention.

One basic element of the kit is a catheter introducer device 100, the general form of which will be familiar to those skilled in the art. The introducer receives a conventional guidewire 102 of conventional diameter, typically around 0.9 mm (0.035 inches). Over the guidewire is then introduced a catheter sheath 104 which embodies the present invention. It has a tapered tip 106 and, just proximal of the tip, a radiopaque platinum-iridium marker band 108 swaged to the outside surface of the tube. At its proximal end is an outward flared tip 110 which mates with a correspondingly frusto-conical receiving surface in a catheter boss 112. This boss has an axial through-bore which, in a distal portion 114 is a snug fit around the outside surface of the catheter tube 104 but in a proximal portion 116 is of larger diameter and is threaded to receive other components of the kit.

Shown in FIG. 3 inside the boss 112 is the sleeve 118 of a stent-introducer device. Within the tube is the self-expanding stent 120 which the delivery device 104 is to deliver. Pushing on the proximal end surface of the stent 120 is a pusher disc 122, itself urged distally by a push rod 124 so that, when the stent 120 is to be introduced into the tube 104 of the delivery device, a compressive stress on the axis of the push rod 124 can urge the compressed stent 120 distally into the proximal end zone 126 of the tube 104 following which the stent introducing device can be detached from the boss 112.

With the stent 120 inside the proximal end of the tube 104, a stent pusher and inner shaft assembly can be offered up to the boss 112 and the proximal end of the tube 104. FIG. 3 shows this inner shaft 130 extending through a sealing boss 132, which is threaded on its outside surface for engagement with the threaded portion of the boss 112. The sealing boss 132 itself carries an internal thread which receives an outside thread on a fluid injection manifold 134, this manifold also having an axial through-bore 136 with a O-ring seal 138 which seals with the inner shaft 130. The fluid injection manifold has a fluid inlet tube 140 which allows injection of liquid into the annular space between the tube 104 and the inner shaft 130, for radiology or for aspiration.

The inner shaft 130 has at its distal end a step defined by a radiopaque marker band 142. Distal of the step is a short distal portion 144 of the length of the inner shaft, which short distal end is in use received within the interior of the stent 120. At the proximal end of the inner shaft 130 is yet another boss 146 by means of which a stent deployment device can engage the inner shaft 30 and apply the appropriate forces as between the outer sheath boss 112 and the inner shaft boss 146, for withdrawal of the outer tube 104 proximally relative to the stent 120, for deployment of the stent in the desired position within the body.

Not shown in FIG. 3 is the lumen within inner shaft 130 on the axis 148 of the inner shaft. This lumen is big enough to receive a protection device, known per se, and as described above, in connection with FIG. 1. FIG. 3 shows various protection devices D, J, K, all located at the distal end of a tube or rod 150 which links the protection device 152 with the medical practitioner at the proximal end of the delivery device. This rod or tube has a diameter which is likely to be in a range of from 0.14 to 0.18 inches.

In use, the catheter introducer is placed percutaneously, as in a Seldinger technique and the guidewire 102 is advanced through the introducer until the figurated distal tip of the guidewire has been manipulated to reach the stenosis. Then, the outer sheath 104 is advanced over the guidewire until its tapered tip 106 is just proximal of the stenosis. The guidewire 102 is then removed. The stent 102 is installed in the proximal end 106 of the tube 104, using the installation device with its tube 118 and push rod 124. After that, the inner shaft 130 is introduced into the proximal end of the tube 104, with its boss 132 in screw fit engagement with the outer sheath boss 112. This then allows progressive advance of the stent 120 along the length of the tube 104 until the stent is just proximal of the distal tip 106. Further steps in the procedure to place the stent are as described above in relation to FIG. 1.

Figure 4:
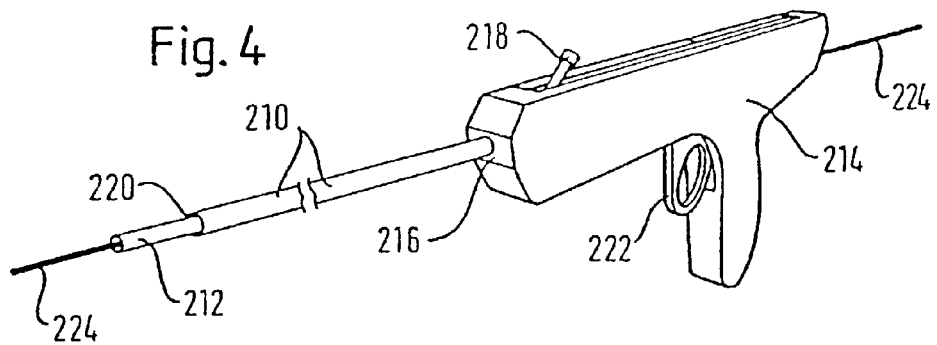
FIG. 4 is a side view of the proximal end of another embodiment of stent delivery system showing a pistol grip stent applicator with inner catheter, outer catheter and guide wire.

FIG. 4 shows the proximal part of another self-expanding stent delivery system. The proximal ends of the outer catheter 210 and inner catheter 212 enter the hand held pistol grip stent applicator 214 at the front end 216. A connection piece 218 provides fluid access to an annular gap 220 between the inner and outer catheter. The outer catheter 210 can be proximally moved from a constraining to a release position with a trigger 222. This system can be manipulated with one hand only. The stent delivery system catheter is advanced along a pre-installed guide wire 224 to the desired location in the bodily lumen. The highly flexible, kink-free catheter tubes are preferably fabricated by co-extrusion of a braiding with polymers such as Nylon or PEBAX. The polymer may advantageously be extruded onto a thin PTFE tube 227. Preferably, this tube extends in the distal direction until a region 229, at which point the diameter of the outer catheter 210 tapers so as to form the tip 226. If desired, a single tube may have sections made of polymers having different hardnesses. Such tubes as such are known in the art.

Figure 5:
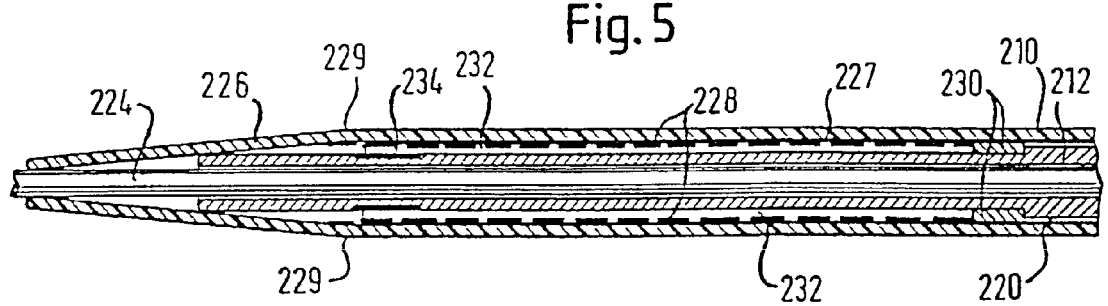
FIG. 5 is a longitudinal axial section of the distal end of the FIG. 4 stent delivery system.
Figure 6:
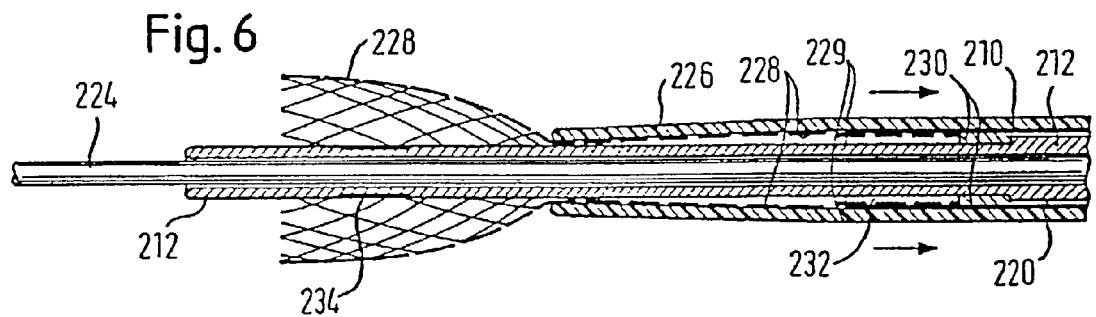
FIG. 6 is a longitudinal axial section of the distal end of the FIG. 4 stent delivery system, similar to that of FIG. 5, depicting the progressive release of a self-expanding stent by moving the unit of tip and outer catheter proximally with respect to the inner catheter.

In FIG. 5 the distal end of the catheter system can be seen. A tapered soft radiopaque tip 226 of a single polymer or a mixture of polymers such as polyurethanes is made in a tip-forming operation, and forms a stepless continuation of the outer catheter 210. The tip angle is preferably in a range of from 5° to 12°. Preferably, a higher hardness of the proximal part of the outer catheter is reduced within a distal transition area to a polymer of lower hardness by changing the extrusion material, for example, two times. The hardness is preferably changed in a range of from 80 Shore D to 40 Shore D. Depending on the requirement of the application one polymer material may be sufficient. The inner catheter 212 is inside the lumen provided by the tip and the outer catheter. The wall thickness of the inner catheter at the distal end is reduced providing a sufficient cavity 232 for the self-expanding stent 228. Preferably, the cavity is made by extruding non-braided material in a pre- or post process onto the proximal braided material of the inner catheter and working it down to the desired recess diameter. A stop ring 230 of 90% platinum and 10% iridium alloy is hammered or swaged down onto the inner catheter 212 at the proximal end of the stent cavity 232. It secures the stent from sliding onto the thicker part, i.e. braided part, of the inner catheter 212, especially while the stent is being inserted into the outer catheter 210 prior to use or during release, as depicted in FIG. 6. It further acts as the proximal marker of the stent. The radiopaque tip 226 enables the operator of the stent delivery system to fix its position in the patient's body. Further, the distal and proximal ends of the stent 228 can be localized by the stop ring 230 and an annular marker 234 of 90% platinum and 10% iridium alloy, see FIG. 5. Tip 226 can be made radiopaque by doping the material, for example, with barium sulfate. The proximal marker 230 and distal marker 234 are hammered or swaged down onto the inner catheter 212. For use with self-expandable stents 228, as depicted in FIG. 5 and 6, whose length shrinks during expansion, the distal marker is located at an appropriate distance proximal to the distal end of the stent, see FIG. 5. The marker 234 indicates the location of the distal end of the stent 228 after full expansion. If the stent suffers no shrinkage in length on expansion, then the location of the distal side of the marker will be at the distal end of the stent also prior to expansion.

In FIG. 6 the tip 226 is pulled proximally onto the stent 228 by pulling the outer catheter 210 by means of the trigger 222 (see FIG. 4) while the position of the inner catheter 212 remains unchanged. The elastic deformation of the tip when being pulled onto the stent-carrying inner catheter creates hoop stress in the soft tip. The stress in the tapered soft tip exerts an annular radial force during the release of the self-expanding stent thereby keeping it in the chosen position and securing it from premature release. The self-expanding stent 228 in FIG. 6 is already half-released and expanded. The distal end of the tip 226 is stretched over the stent and squeezes the stent mid-way along its length.

Figure 7:
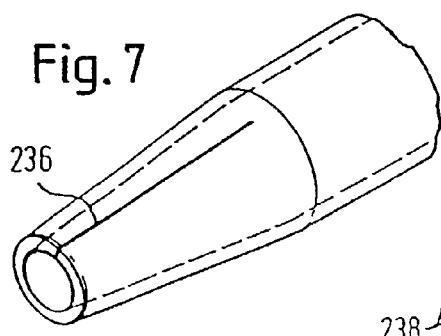
FIG. 7 is a perspective view of a first embodiment of the tapered tip, showing one slit of several spaced slits parallel to its axis.
Figure 8:
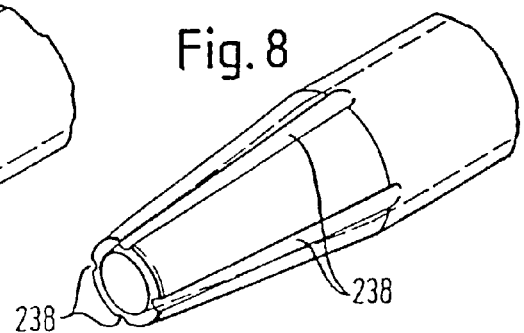
FIG. 8 is a perspective view of a second embodiment of the tapered tip showing four axis-parallel elongate thickness reduction zones lying parallel to the axis.

FIGS. 7 and 8 show two embodiments of tips with axially-oriented zones of reduced resistance to radially-outward deformation, i.e. stretch zones. One embodiment features an axially oriented slit 236 shown in FIG. 7. Another embodiment features axis parallel thickness reduction zones 238, shown in FIG. 8. Such tips are particularly suitable for use with stents of relatively large diameter. The number of stretch zones may vary corresponding to the stent size, for example from 1 to 4, but preferred is a symmetric arrangement of said zones.

Figure 9:
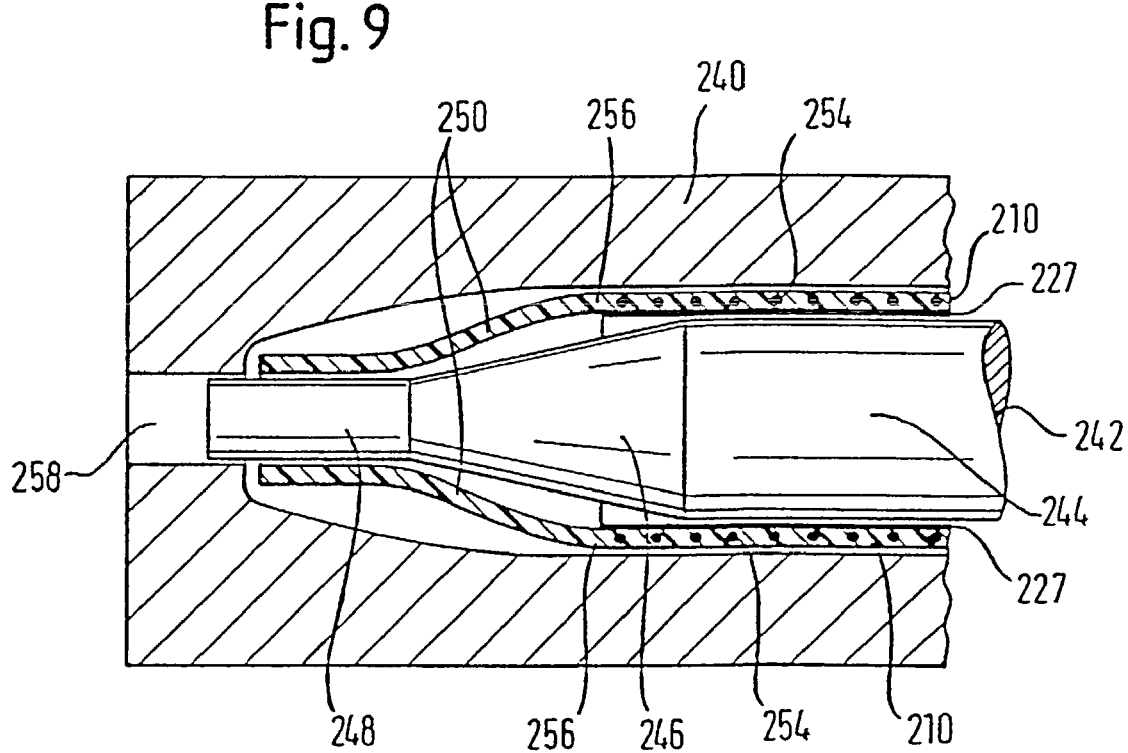
FIG. 9 is a longitudinal axial section through a first embodiment of mold and mandrel for forming the tip of a sleeve pre-form.

FIG. 9 shows a mold 240 and a mandrel 242 obtainable from SEBRA, Engineering & Research Associates Inc., Tucson, USA, for the tip-shaping operation. The mandrel 242 has a main body 244, a section for forming the tip 246 and a cylindrical distal tip-section 248. The distal section of the outer catheter 210 is necked down to create a pre-form 250 shaped like a bottleneck. Preferably, the braiding 254 and the inner PTFE-lining 227 of the outer catheter 210 extend distally to the proximal end 256 of the necked down section whereof the tip is be formed. For the tip-shaping operation of the pre-form 250 the mandrel 242 is advanced from the proximal to the distal end of the outer catheter 210 until the cylindrical section 248 projects distally out of the pre-form 250. Then, the mandrel 242, together with the pre-form 250, is inserted into the hollow mold 240. The mandrel 242 is first centered by inserting the cylindrical tip-section 248 into a corresponding bore 258 of the hollow mold 240, in which it is a snug fit. Then the distal end of the pre-form 250 is advanced until it touches the inner wall of the hollow mold 240. For forming the final tip shape in the mold cavity, the mold 240 is heated, to thermoform the tip shape in the cavity between the mold 240 and the mandrel 242. During this heating phase the mandrel 242 is pressed into the hollow mold to form the final tip. The form closure between the cylinder 248 of the mandrel and the respective opening 250 prevents the leaking of material out of the molding section. The forming during the heating phase is followed by a cooling phase before the mandrel 242 is withdrawn proximally and the formed tip is taken out of the hollow mould.

Figure 10:
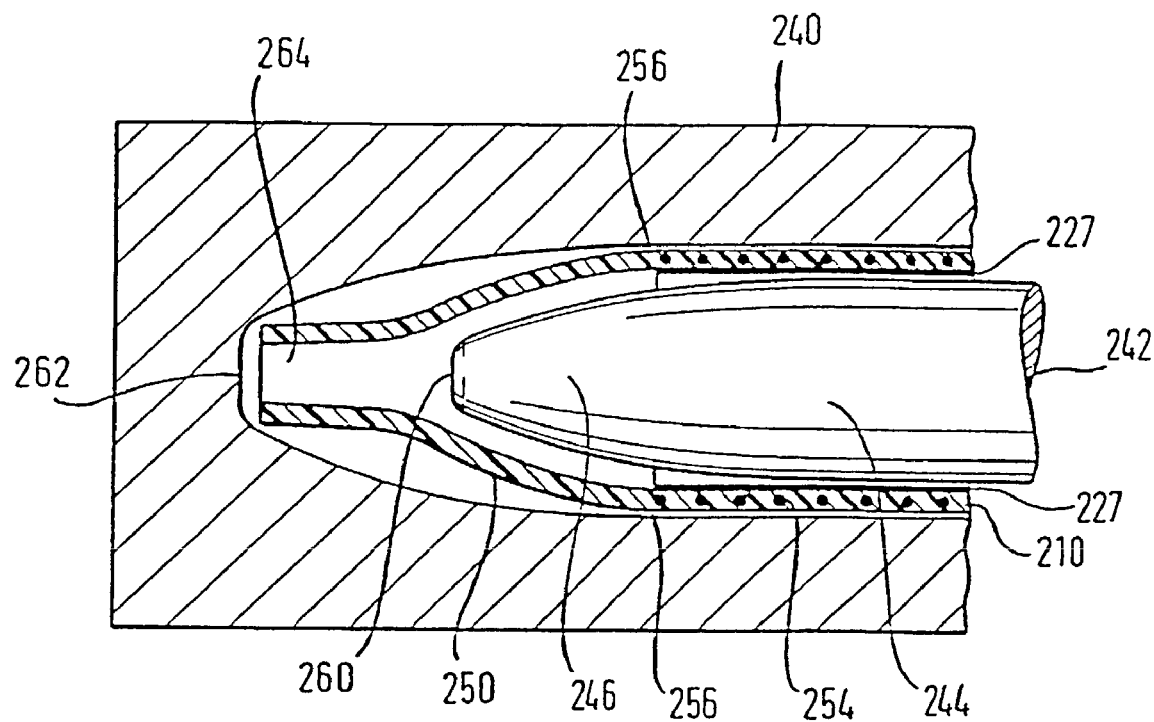
FIG. 10 is a similar section of a second embodiment of mold and mandrel for tip forming.
Figure 11:
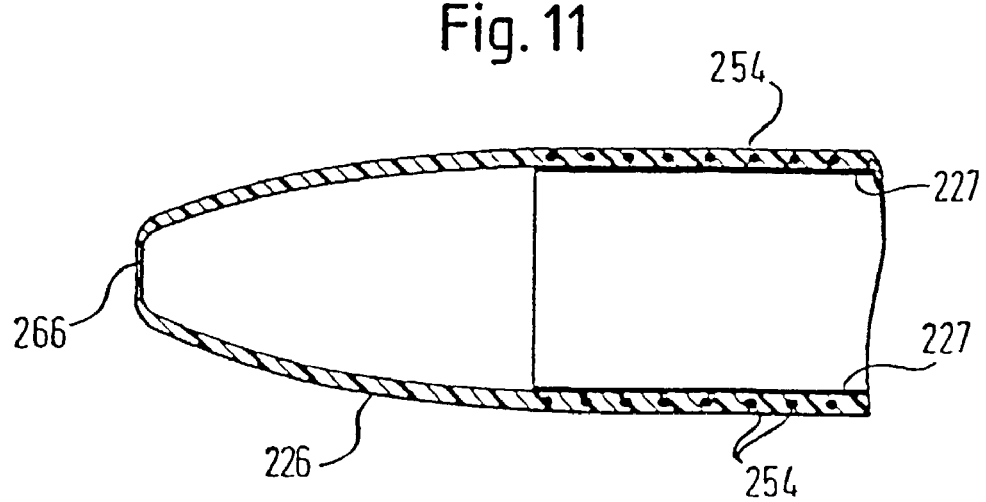
FIG. 11 is a section through a tip formed by the FIG. 10 mold and mandrel.

In FIGS. 10 and 11 like reference numbers are used to indicate components which have counterparts in the FIG. 9 embodiment. These will not be described again.

The hollow mold 240 of FIGS. 10 and 11 has a cavity which terminates in an end wall 262 which will define the outside surface of a membrane 266 to be seen in the formed tip shown in FIG. 11. A mandrel or mold insert 242 is also formed with an end wall 260 and, when the mandrel is advanced into the mold cavity it is arranged that there is a thin gap between the facing end wall surfaces 260 and 262, which thereby define the thickness of the membrane 266.

The membrane is thin enough to rupture when required, when a stent is being deployed, or when the catheter is to be advanced over a pre-placed guide wire the proximal end of which penetrates the membrane from a position distal of the membrane.

INDUSTRIAL APPLICATION

As explained above, the present invention removes some of the constraints on diameters of stent delivery systems and stents in the compact configuration of the stent prior to deployment. Specifically, when the task is for delivery of a stent having a particular diameter in its compact disposition, the present invention opens up possibilities for construction of a delivery system which is of smaller diameter than the systems hitherto used to place a stent of that given diameter. The invention also offers possibilities to simplify the composition of a procedure kit for placing any particular stent, specifically, by reducing the number of elements required in that kit. Whereas previously it has been the practice to place a stent radially inside the tube of a stent delivery system, and then place that tube inside the lumen of a guide catheter, the present invention opens up the possibility to place the stent directly inside the lumen of the guide catheter, thereby saving the space which would otherwise have been occupied by the stent-confining tube of the stent delivery system, separate from the guide catheter.

The invention claimed is:

1. A percutaneous, transluminal stent delivery system, comprising:
 a tube for insertion into a body having a tube wall and extending a length between a proximal end and a distal end at a distal end of the system, the tube including luminal and abluminal surfaces and defining a lumen which extends the full length of the tube from a flare end to a distal tip zone contiguous with and affixed to the distal end of the tube, the distal tip zone including both the luminal surface and the abluminal surface tapering radially inwardly with increasing nearness to the distal end of the tube; and
 a device to advance a stent constrained from radially-outward expansion by the tube wall, at least a portion of the device being disposed in the lumen of the tube between the proximal end of the tube and the distal end of the tube, the device being removable from the flare end of the tube,
 wherein the distal tip zone is configured and attached to the distal end of the tube such that proximally withdrawing the distal end of the tube over the stent proximally withdraws the distal tip zone over the stent.

2. A percutaneous, transluminal stent delivery system, comprising:
 a tube for insertion into a body having a tube wall and extending a length between a proximal end and a distal end at a distal end of the system, the tube including luminal and abluminal surfaces and defining a lumen which extends the full length of the tube from a flare end to a distal tip zone contiguous with and affixed to the distal end of the tube, the distal tip zone including both the luminal surface and the abluminal surface tapering radially inwardly with increasing nearness to the distal end of the tube; and
 a device to advance a stent constrained from radially-outward expansion by the tube wall, at least a portion of the device being disposed in the lumen of the tube between the proximal end of the tube and the distal end of the tube, the device being removable from the flare end of the tube,
 wherein the distal tip zone is configured and attached to the distal end of the tube such that distally advancing the stent past the distal end of the tube proximally withdraws the distal tip zone over the stent.

3. A percutaneous, transluminal stent delivery system, comprising:
 a tube for insertion into a body having a tube wall and extending a length between a proximal end and a distal end at a distal end of the system, the tube including luminal and abluminal surfaces and defining a lumen which extends the full length of the tube from a flare end to a distal tip zone contiguous with and affixed to the distal end of the tube, the distal tip zone including both the luminal surface and the abluminal surface tapering radially inwardly with increasing nearness to the distal end of the tube;
 a device to advance a stent constrained from radially-outward expansion by the tube wall, at least a portion of the device being disposed in the lumen of the tube between the proximal end of the tube and the distal end of the tube, the device being removable from the flare end of the tube; and
 means for introducing into the proximal end of the tube a fluid,
 wherein the distal tip zone is configured and attached to the distal end of the tube such that proximally withdrawing the distal end of the tube over the stent proximally withdraws the distal tip zone over the stent.

4. A percutaneous, transluminal stent delivery system, comprising:
 a tube for insertion into a body having a tube wall and extending a length between a proximal end and a distal end at a distal end of the system, the tube including luminal and abluminal surfaces and defining a lumen which extends the full length of the tube from a flare end to a distal tip zone contiguous with and affixed to the distal end of the tube, the distal tip zone including both the luminal surface and the abluminal surface tapering radially inwardly with increasing nearness to the distal end of the tube;

a device to advance a stent constrained from radially-outward expansion by the tube wall, at least a portion of the device being disposed in the lumen of the tube between the proximal end of the tube and the distal end of the tube, the device being removable from the flare end of the tube; and means for introducing into the proximal end of the tube a fluid, wherein the distal tip zone is configured and attached to the distal end of the tube such that distally advancing the stent past the distal end of the tube proximally withdraws the distal tip zone over the stent.

5. A percutaneous, transluminal stent delivery system, comprising:

a tube for insertion into a body having a tube wall and extending a length between a proximal end and a distal end at a distal end of the system, the tube including luminal and abluminal surfaces and defining a lumen, the tube having a proximal flared end and a distal tip zone attached to the distal end of the tube, the distal tip zone including both the luminal surface and the abluminal surface tapering radially inwardly with increasing nearness to the distal end of the tube; and a device to advance a stent constrained from radially-outward expansion by the tube wall, at least a portion of the device being disposed in the lumen of the tube between the proximal end of the tube and the distal end of the tube, the device being removable from the flare end of the tube, wherein the distal tip zone is configured and attached to the distal end of the tube such that proximally withdrawing the distal end of the tube over the stent proximally withdraws the distal tip zone over the stent.

6. A percutaneous, transluminal stent delivery system, comprising:

a tube for insertion into a body having a tube wall and extending a length between a proximal end and a distal end at a distal end of the system, the tube including luminal and abluminal surfaces and defining a lumen, the tube having a proximal flared end and a distal tip zone attached to the distal end of the tube, the distal tip zone including both the luminal surface and the abluminal surface tapering radially inwardly with increasing nearness to the distal end of the tube; and a device to advance a stent constrained from radially-outward expansion by the tube wall, at least a portion of the device being disposed in the lumen of the tube between the proximal end of the tube and the distal end of the tube, the device being removable from the flare end of the tube, wherein the distal tip zone is configured and attached to the distal end of the tube such that distally advancing the stent past the distal end of the tube proximally withdraws the distal tip zone over the stent.

\* \* \* \* \*